United States Patent
Ruckdeschel et al.

(10) Patent No.: US 8,887,722 B2
(45) Date of Patent: Nov. 18, 2014

(54) INHALER MECHANISMS WITH RADIALLY BIASED PIERCERS AND RELATED METHODS

(75) Inventors: Thomas W. Ruckdeschel, Cary, NC (US); David Harris, Milton (GB)

(73) Assignee: Oriel Therapeutics, Inc., Durham, NC (US)

( * ) Notice: Subject to any disclaimer, the term of this patent is extended or adjusted under 35 U.S.C. 154(b) by 879 days.

(21) Appl. No.: 13/063,527

(22) PCT Filed: Sep. 25, 2009

(86) PCT No.: PCT/US2009/005321
§ 371 (c)(1),
(2), (4) Date: Mar. 11, 2011

(87) PCT Pub. No.: WO2010/036355
PCT Pub. Date: Apr. 1, 2010

(65) Prior Publication Data
US 2011/0162648 A1 Jul. 7, 2011

Related U.S. Application Data

(60) Provisional application No. 61/148,520, filed on Jan. 30, 2009, provisional application No. 61/102,073, filed on Oct. 2, 2008, provisional application No. 61/100,482, filed on Sep. 26, 2008.

(51) Int. Cl.
*A61M 15/00* (2006.01)
*A61M 16/00* (2006.01)

(52) U.S. Cl.
CPC ....... *A61M 15/0045* (2013.01); *A61M 15/0048* (2014.02); *A61M 15/0041* (2014.02); *A61M 15/0075* (2014.02); *A61M 2202/064* (2013.01)
USPC .................................................. 128/203.21

(58) Field of Classification Search
USPC .................... 222/81–91; 128/203.15, 203.12, 128/200.17, 200.14, 203.21
See application file for complete search history.

(56) References Cited

U.S. PATENT DOCUMENTS

| 2,828,005 A | 3/1958 | Ricke |
| 4,307,734 A | 12/1981 | Blankenship |

(Continued)

FOREIGN PATENT DOCUMENTS

| CA | 2506866 A1 * | 6/2004 |
| DE | 19500764 | 7/1996 |

(Continued)

OTHER PUBLICATIONS

International Search Report and Written Opinion for corresponding PCT Application No. PCT/US2009/005321, date of mailing Mar. 29, 2010.

(Continued)

*Primary Examiner* — Jackie T Ho
*Assistant Examiner* — Mark Wardas
(74) *Attorney, Agent, or Firm* — Myers Bigel Sibley & Sajovec, P.A.

(57) ABSTRACT

Inhalers with an inhaler housing having a dose container disk having inner and outer perimeters mounted in the housing. The dose container disk has a plurality of circumferentially spaced apart dose containers with dry powder therein. The inhalers also include a piercer carriage with a piercer mounted in the inhaler. The piercer carriage is in communication with a resilient member that radially biases the piercer carriage to radially travel to align the piercer with an underlying or overlying dose container.

15 Claims, 33 Drawing Sheets

(56) References Cited

U.S. PATENT DOCUMENTS

| | | |
|---|---|---|
| 4,627,432 A | 12/1986 | Newell et al. |
| 4,778,054 A | 10/1988 | Newell et al. |
| 4,811,731 A | 3/1989 | Newell et al. |
| 5,035,237 A | 7/1991 | Newell et al. |
| 5,138,138 A | 8/1992 | Theilacker et al. |
| 5,327,883 A | 7/1994 | Williams et al. |
| 5,337,740 A | 8/1994 | Armstrong et al. |
| 5,388,572 A | 2/1995 | Mulhauser et al. |
| 5,394,868 A | 3/1995 | Ambrosio et al. |
| 5,529,059 A | 6/1996 | Armstrong et al. |
| 5,533,502 A | 7/1996 | Piper |
| 5,590,645 A | 1/1997 | Davies et al. |
| 5,622,166 A | 4/1997 | Eisele et al. |
| 5,634,900 A | 6/1997 | Makino et al. |
| 5,715,810 A | 2/1998 | Armstrong et al. |
| 5,727,607 A | 3/1998 | Ichikawa et al. |
| 5,769,073 A | 6/1998 | Eason et al. |
| 5,860,419 A | 1/1999 | Davies et al. |
| 5,873,360 A | 2/1999 | Davies et al. |
| 5,909,829 A | 6/1999 | Wegman et al. |
| 5,921,237 A | 7/1999 | Eisele et al. |
| 5,947,169 A | 9/1999 | Wegman et al. |
| 6,029,663 A | 2/2000 | Eisele et al. |
| 6,032,666 A | 3/2000 | Davies et al. |
| 6,082,356 A | 7/2000 | Stradella |
| 6,116,238 A | 9/2000 | Jackson et al. |
| 6,245,339 B1 | 6/2001 | Van Oort et al. |
| 6,328,033 B1 | 12/2001 | Avrahami |
| 6,367,473 B1 | 4/2002 | Käfer |
| 6,378,519 B1 | 4/2002 | Davies et al. |
| 6,445,941 B1 | 9/2002 | Hampton et al. |
| 6,536,427 B2 | 3/2003 | Davies et al. |
| 6,543,448 B1 | 4/2003 | Smith et al. |
| 6,550,477 B1 | 4/2003 | Casper et al. |
| 6,591,832 B1 | 7/2003 | DeJonge |
| 6,655,381 B2 | 12/2003 | Keane et al. |
| 6,668,827 B2 | 12/2003 | Schuler et al. |
| 6,679,254 B1 | 1/2004 | Rand et al. |
| 6,792,945 B2 | 9/2004 | Davies et al. |
| 6,810,872 B1 | 11/2004 | Ohki et al. |
| 6,871,647 B2 | 3/2005 | Allan et al. |
| 6,880,555 B1 | 4/2005 | Brunnberg et al. |
| 6,889,690 B2 | 5/2005 | Crowder et al. |
| 6,915,802 B1 | 7/2005 | Anderson et al. |
| 6,923,178 B2 | 8/2005 | Snow |
| 6,948,494 B1 | 9/2005 | Snow |
| 7,089,935 B1 | 8/2006 | Rand |
| 7,219,665 B1 | 5/2007 | Braithwaite |
| 7,225,808 B2 | 6/2007 | Davies et al. |
| 7,275,538 B2 | 10/2007 | Nakamura |
| 7,318,436 B2 * | 1/2008 | Snow ............... 128/203.21 |
| 7,389,775 B2 | 6/2008 | Davies et al. |
| 7,503,324 B2 | 3/2009 | Barney et al. |
| 7,571,723 B2 | 8/2009 | Braithwaite |
| 7,571,724 B2 | 8/2009 | Braithwaite |
| 7,669,597 B2 | 3/2010 | Sullivan et al. |
| 8,037,880 B2 | 10/2011 | Zhu et al. |
| 8,381,721 B2 | 2/2013 | Thoe et al. |
| 2001/0007853 A1 | 7/2001 | Dimarchi et al. |
| 2001/0053761 A1 | 12/2001 | Dimarchi et al. |
| 2002/0040713 A1 | 4/2002 | Eisele et al. |
| 2002/0170560 A1 | 11/2002 | Young et al. |
| 2003/0178024 A1 | 9/2003 | Allan et al. |
| 2004/0025877 A1 | 2/2004 | Crowder et al. |
| 2005/0056281 A1 | 3/2005 | Snow |
| 2005/0126568 A1 | 6/2005 | Davies et al. |
| 2005/0154491 A1 | 7/2005 | Anderson et al. |
| 2005/0161041 A1 | 7/2005 | Schuler et al. |
| 2005/0172963 A1 | 8/2005 | Allan et al. |
| 2006/0102511 A1 | 5/2006 | Pasbrig et al. |
| 2006/0157053 A1 | 7/2006 | Barney et al. |
| 2007/0062525 A1 | 3/2007 | Bonney et al. |
| 2007/0137643 A1 | 6/2007 | Bonney et al. |
| 2007/0137645 A1 | 6/2007 | Eason et al. |
| 2007/0181123 A1 | 8/2007 | Houzego |
| 2007/0181124 A1 | 8/2007 | Casper et al. |
| 2007/0215149 A1 | 9/2007 | King et al. |
| 2007/0221218 A1 | 9/2007 | Warden et al. |
| 2007/0235029 A1 | 10/2007 | Zhu et al. |
| 2008/0001008 A1 | 1/2008 | Thoemmes et al. |
| 2008/0127971 A1 | 6/2008 | King et al. |
| 2008/0223366 A1 | 9/2008 | Davies et al. |
| 2009/0114220 A1 | 5/2009 | Wachtel et al. |
| 2009/0139516 A1 | 6/2009 | Augustyn et al. |
| 2009/0194105 A1 | 8/2009 | Besseler et al. |
| 2010/0078022 A1 | 4/2010 | Striebig et al. |
| 2010/0163042 A1 * | 7/2010 | Bhowmick et al. ...... 128/203.15 |

FOREIGN PATENT DOCUMENTS

| | | |
|---|---|---|
| EP | 1106196 | 3/2001 |
| EP | 1 779 884 A1 | 5/2007 |
| EP | 1844805 | 10/2007 |
| GB | 873410 | 7/1961 |
| GB | 2246299 | 3/1992 |
| GB | 2340758 | 3/2000 |
| JP | 2001-161820 A | 6/2001 |
| WO | WO 94/14490 | 7/1994 |
| WO | WO 94/20164 | 9/1994 |
| WO | WO 98/30263 A1 | 7/1998 |
| WO | WO 98/41265 | 9/1998 |
| WO | WO 98/41265 A1 | 9/1998 |
| WO | WO 99/36116 | 7/1999 |
| WO | WO 00/45879 | 8/2000 |
| WO | WO 01/17595 | 3/2001 |
| WO | WO 01/28616 | 4/2001 |
| WO | WO 01/34234 | 5/2001 |
| WO | WO 02/053215 | 7/2002 |
| WO | WO 02/053216 | 7/2002 |
| WO | WO 03/011708 | 2/2003 |
| WO | WO 2004/045487 | 6/2004 |
| WO | WO 2005/002654 | 1/2005 |
| WO | WO 2005/002654 A2 | 1/2005 |
| WO | WO 2005/037353 | 4/2005 |
| WO | WO 2005/044173 | 5/2005 |
| WO | WO 2005/110519 | 11/2005 |
| WO | WO 2006/031775 | 3/2006 |
| WO | WO 2006/108877 | 10/2006 |
| WO | WO 2007/007110 | 1/2007 |
| WO | WO 2007/012871 | 2/2007 |
| WO | WO 2007/118648 A1 | 10/2007 |
| WO | WO 2008/039182 A1 | 4/2008 |

OTHER PUBLICATIONS

Hickey et al., A new millennium for inhaler technology, 21 Pharm. Tech., n. 6, pp. 116-125 (1997).

Prime et al., Review of Dry Powder Inhalers, 26 Adv. Drug Delivery Rev., pp. 51-58 (1997).

Wolff et al., Generation of Aerosolized Drugs, J. Aerosol. Med., pp. 88-106 (1994).

* cited by examiner

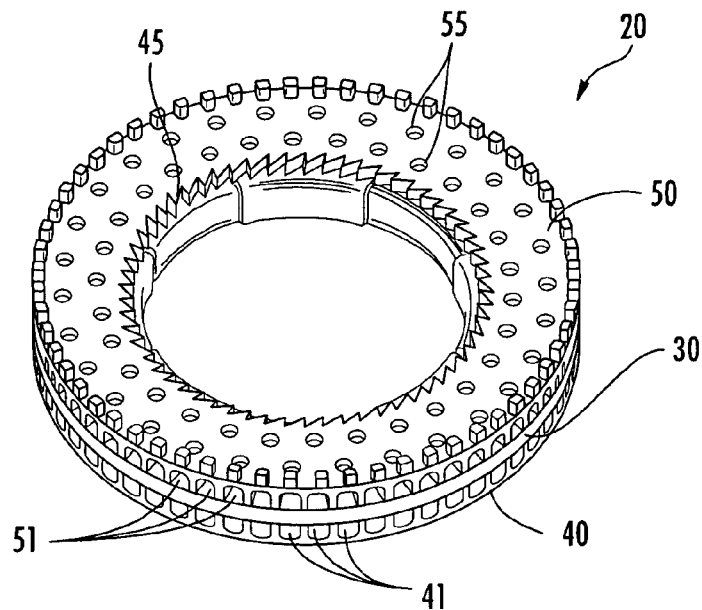
FIG. 2A
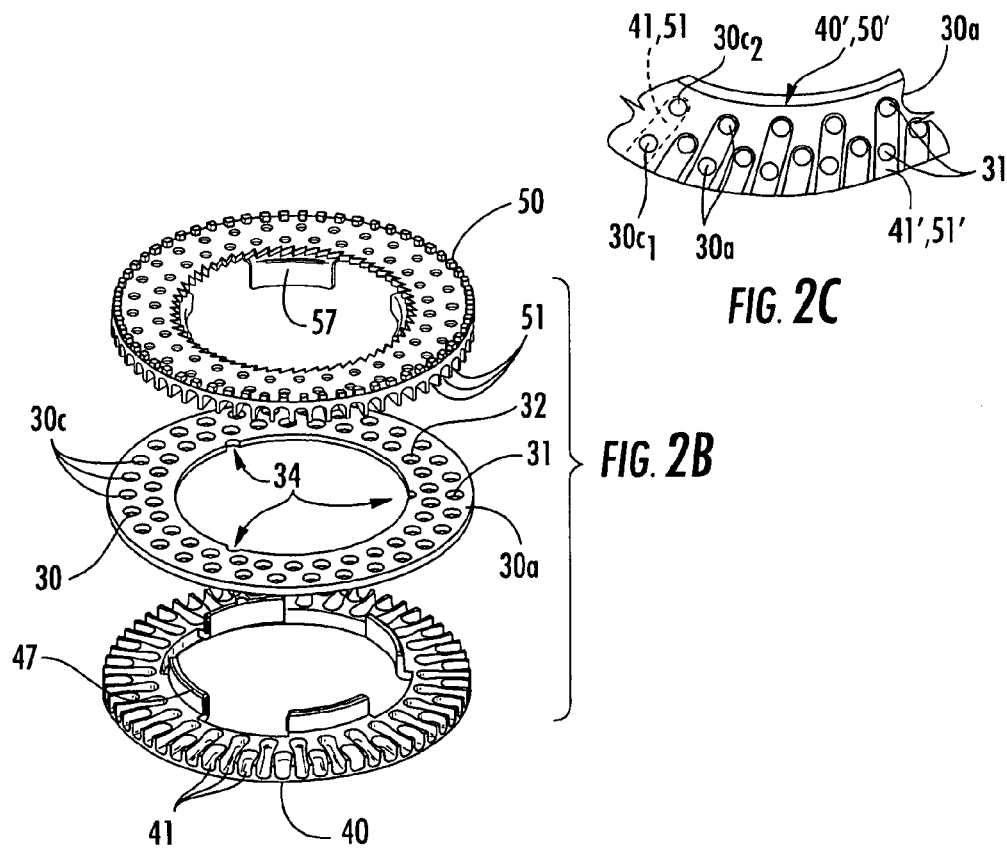
FIG. 2C
FIG. 2B

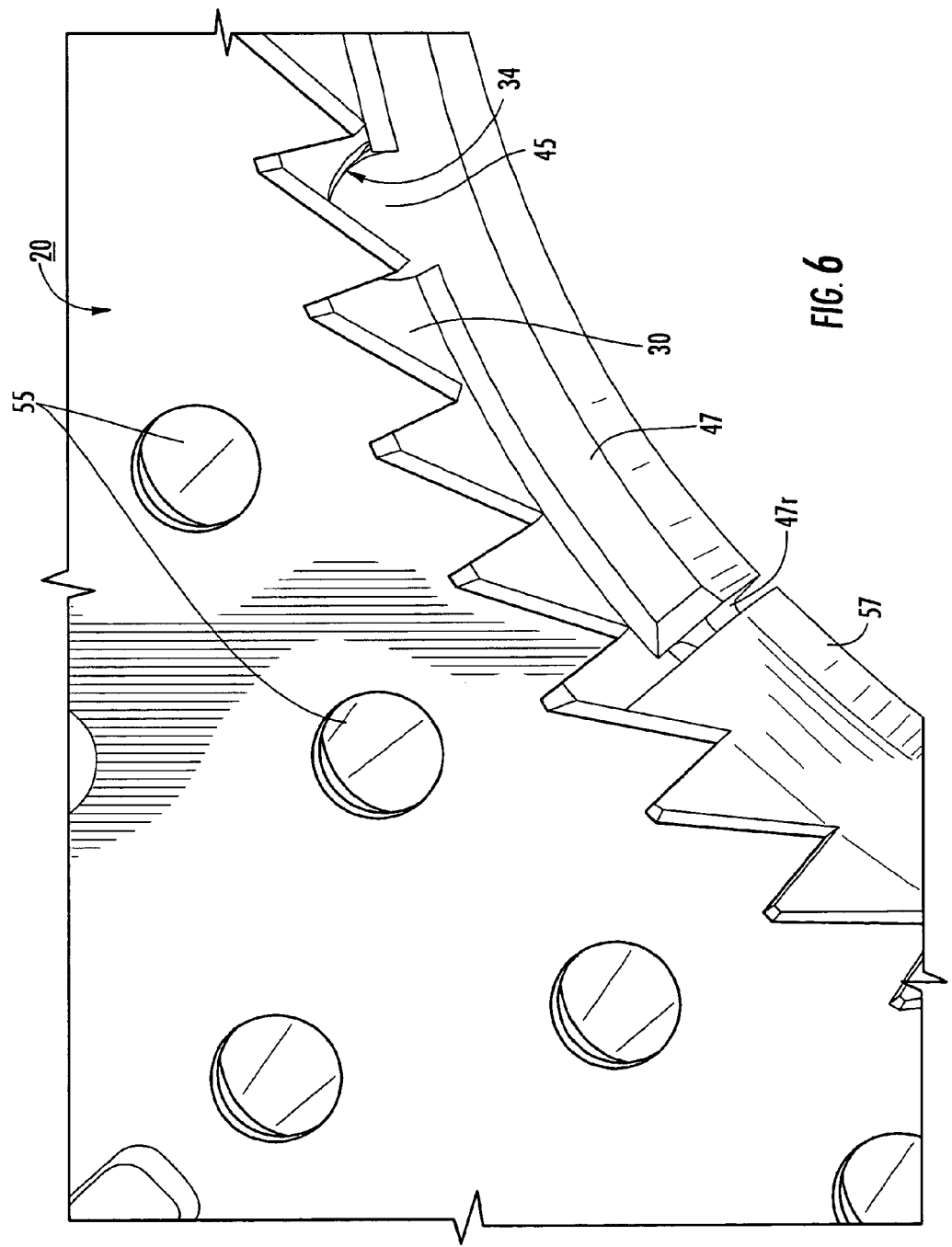

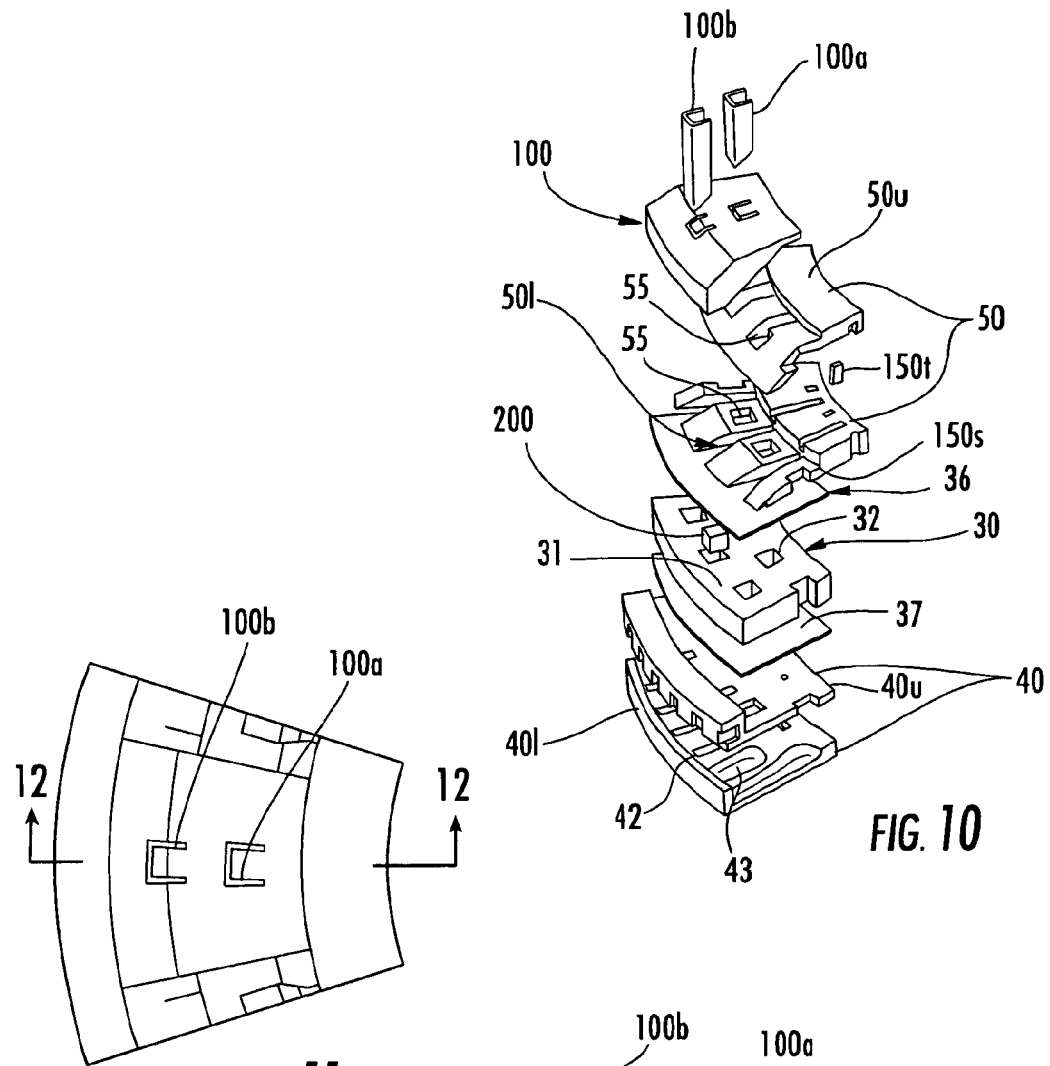
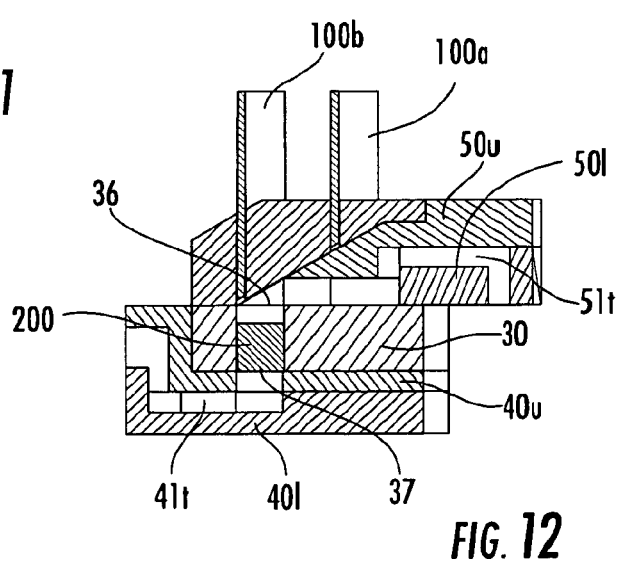
FIG. 10
FIG. 11
FIG. 12

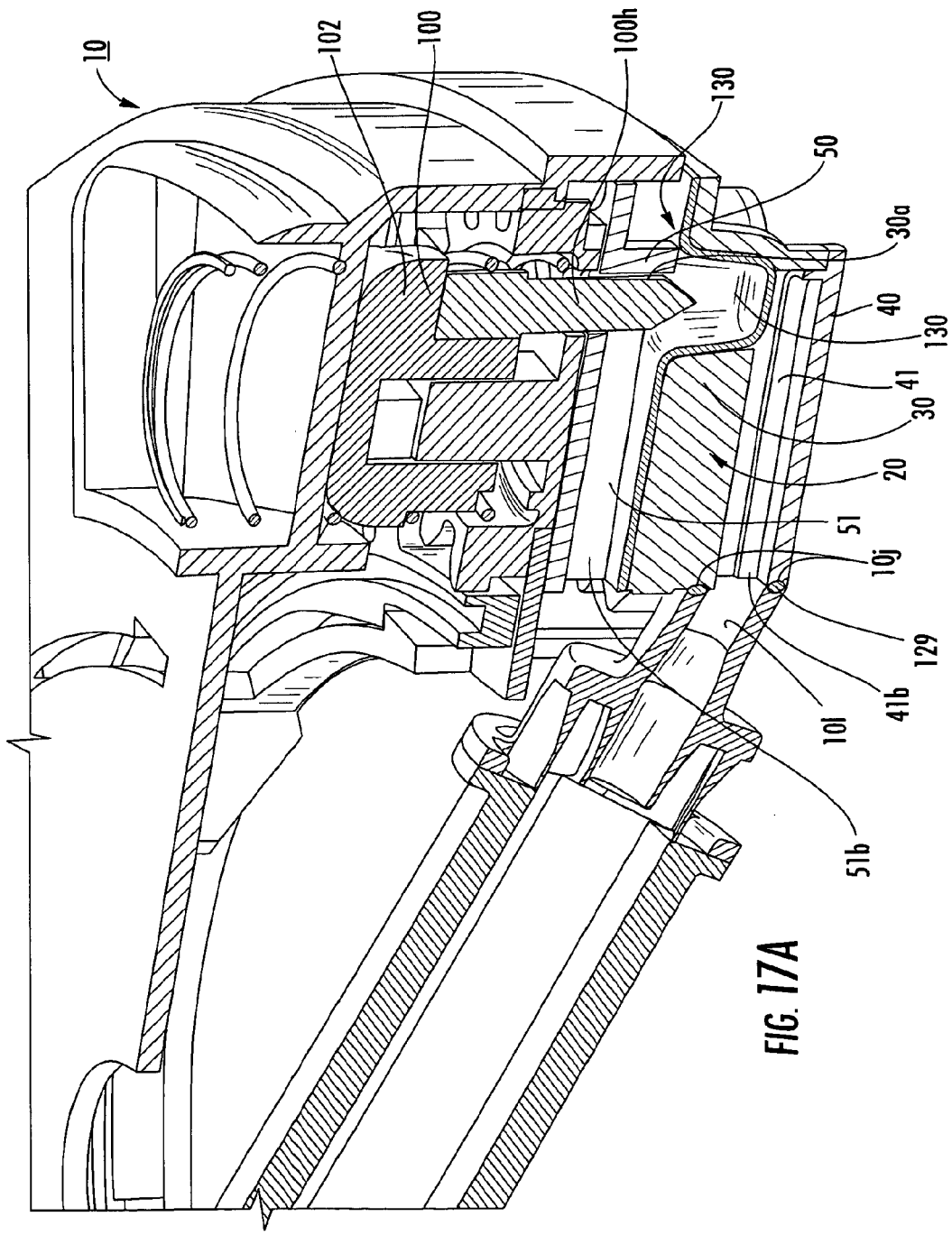

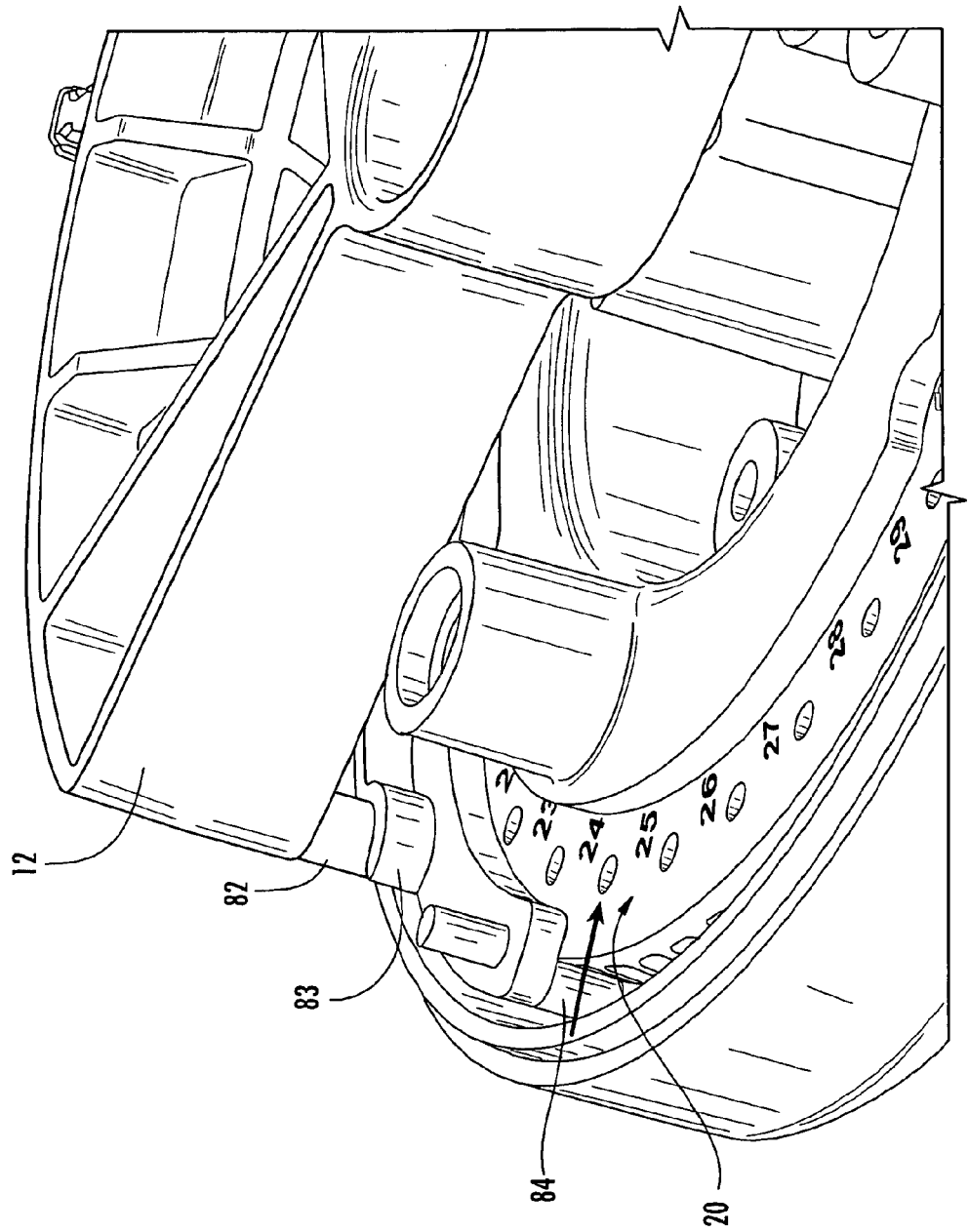

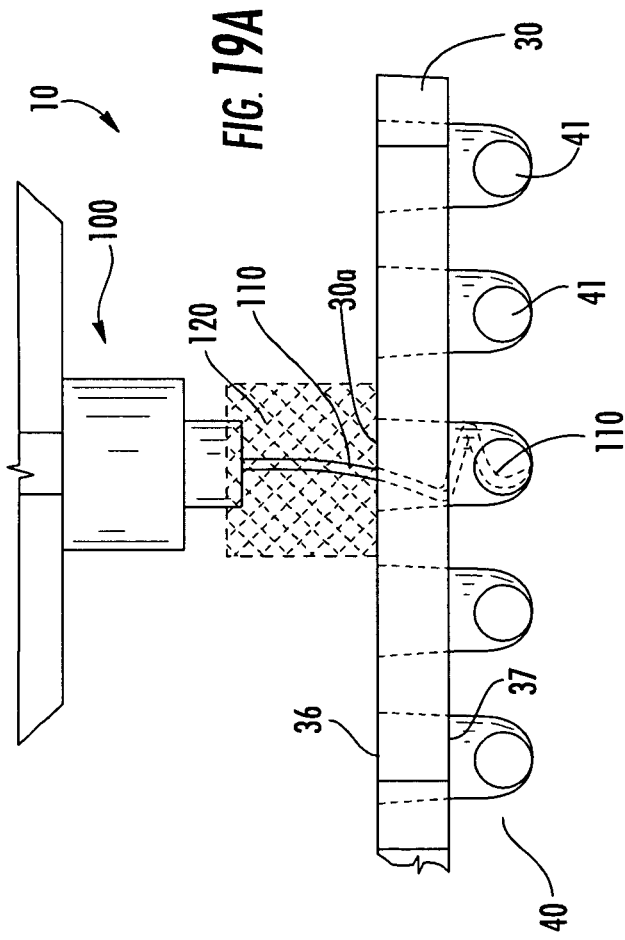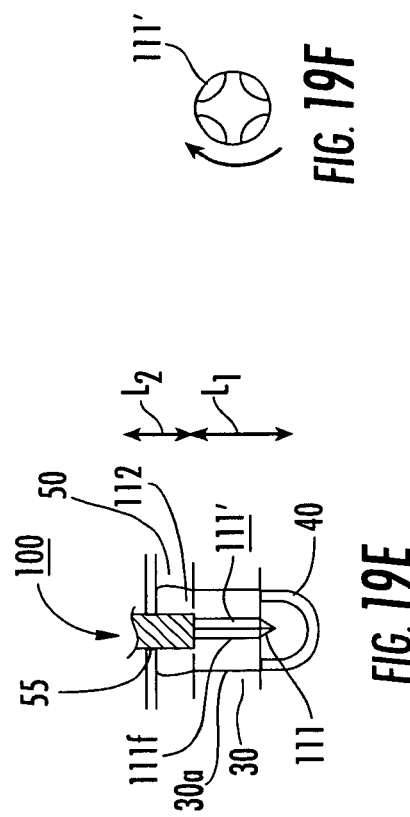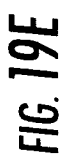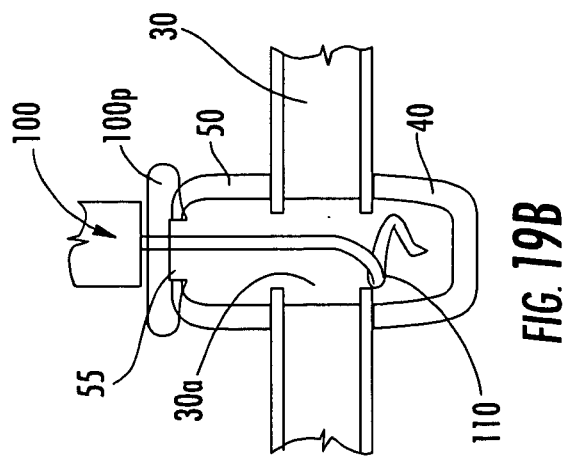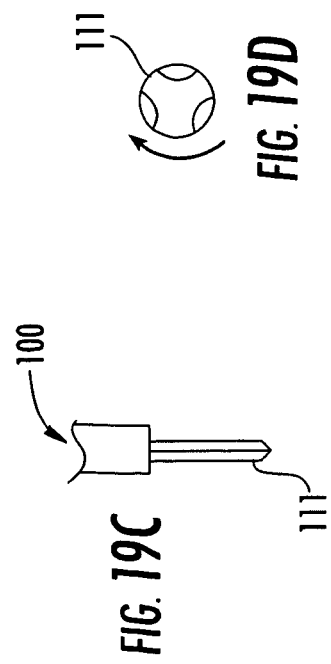

```
┌─────────────────────────┐
│ PROVIDING A DOSE CONTAINER│
│ RING HAVING STAGGERED    │
│ CONCENTRIC DOSE CONTAINER│
│ APERTURES SEALED BY UPPER│         ┌─ ─ ─ ─ ─ ─ ─ ─ ─ ─ ─ ─ ─ ─ ─┐
│ AND LOWER SEALANT LAYERS │         │ ADVANCING A PIERCING        │
│ ATTACHED TO AN UNDERLYING│         │ MECHANISM TO OPEN BOTH      │
│ DISK HAVING A PLURALITY OF│        │ SEALANT LAYERS AND RELEASE  │
│ CIRCUMFERENTIALLY SPACED │─ ─ ─ ─ ─▶│ DRY POWDER FROM THE DOSE   │
│ APART AIRWAY CHANNELS, ONE│        │ CONTAINER TO THE RESPECTIVE │
│ FOR EACH DOSE CONTAINER. │         │ AIRWAY CHANNEL.             │
│ 300                      │         │ 320                          │
└─────────────────────────┘         └─ ─ ─ ─ ─ ─ ─ ─ ─ ─ ─ ─ ─ ─ ─┘
              │                                    │
              ▼                                    │
┌─────────────────────────┐         ┌─ ─ ─ ─ ─ ─ ─ ─ ─ ─ ─ ─ ─ ─ ─┐
│ ROTATING THE DOSE CONTAINER│       │ FULLY RETRACTING THE PIERCING│
│ RING WITH THE UNDERLYING DISK│◀─ ─ │ MECHANISM FROM THE DOSE      │
│ TO A DISPENSING POSITION IN │     │ CONTAINER APERTURE           │
│ THE INHALER.              │       │                              │
│ 310                       │       │ 350                          │
└─────────────────────────┘         └─ ─ ─ ─ ─ ─ ─ ─ ─ ─ ─ ─ ─ ─ ─┘
              │                                    ▲
              ▼                                    │
┌─────────────────────────┐                        │
│ ISOLATING THE AIRWAY CHANNEL│                    │
│ ASSOCIATED WITH THE OPENED │                     │
│ DOSE CONTAINER FROM AN     │                     │
│ INHALATION AIRFLOW PATH SO THAT│─ ─ ─ ─ ─ ─ ─ ─ ─┘
│ THE USED AIRFLOW CHANNEL IS│
│ NOT USED FOR ANY SUBSEQUENT│
│ INHALATION DELIVERY OR IS RE-│
│ USED ONLY ONCE.            │
│ 325                        │
└─────────────────────────┘
```

FIG. 20

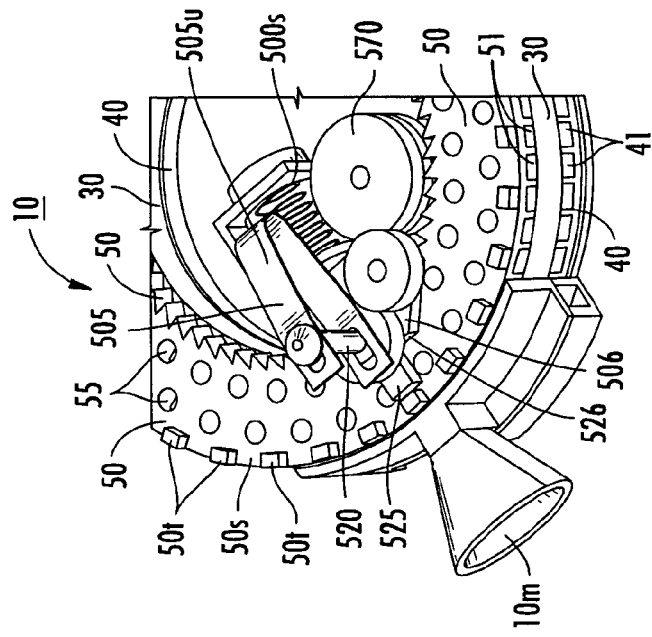
FIG. 22A
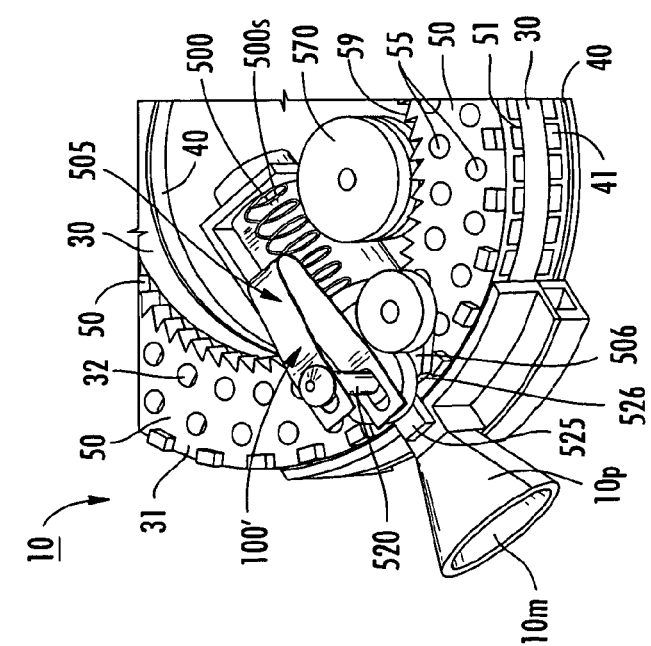
FIG. 22B
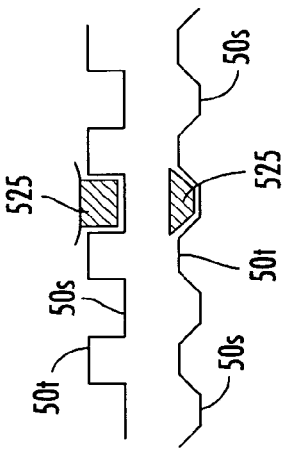
FIG. 23A
FIG. 23B

INHALER MECHANISMS WITH RADIALLY BIASED PIERCERS AND RELATED METHODS

RELATED APPLICATIONS

This application is a 35 USC 371 national phase application of PCT/US2009/005321, filed Sep. 25, 2009, which claims the benefit of and priority to U.S. Provisional Application Ser. No. 61/100,482, filed Sep. 26, 2008, U.S. Provisional Application Ser. No. 61/102,073 filed Oct. 2, 2008, and U.S. Provisional Application Ser. No. 61/148,520, filed Jan. 30, 2009, the contents of which are hereby incorporated by reference as if recited in full herein.

FIELD OF THE INVENTION

The present invention relates to inhalers, and may be particularly suitable for dry powder inhalers.

BACKGROUND OF THE INVENTION

Generally described, known single and multiple dose Dry Powder Inhalers (DPIs) are an established alternative to pressurized metered dose inhalers (pMDIs). DPIs can use: (a) individual pre-measured doses in blisters containing the drug, which can be inserted into the device prior to dispensing; or (b) bulk powder reservoirs which are configured to administer successive quantities of the drug to the patient via a dispensing chamber which dispenses the proper dose. See generally Prime et al., *Review of Dry Powder Inhalers*, 26 Adv. Drug Delivery Rev., pp. 51-58 (1997); and Hickey et al., *A new millennium for inhaler technology*, 21 Pharm. Tech., n. 6, pp. 116-125 (1997).

In operation, DPI devices strive to administer a uniform aerosol dispersion amount in a desired physical form of the dry powder (such as a particulate size or sizes) into a patient's airway and direct it to a desired internal deposit site(s).

Despite the above, there remains a need for alternate inhaler configurations and/or opening mechanisms.

SUMMARY OF EMBODIMENTS OF THE INVENTION

Embodiments of the invention provide radially-biased piercers that can open dose containers in an inhaler.

Some embodiments are directed to inhalers with an inhaler housing having a dose container disk having inner and outer perimeters mounted in the housing. The dose container disk has a plurality of circumferentially spaced apart dose containers with dry powder therein. The inhalers also include a piercer carriage with a piercer mounted in the inhaler. The piercer carriage is in communication with a resilient member that radially biases the piercer carriage to radially travel to align the piercer with an underlying or overlying dose container (typically alternating between inner and outer rows of dose containers, where disks having multiple row dose containers are used).

The piercer carriage can include a platform that resides over or under the dose container disk and communicates with the resilient member. The platform can include an aperture extending therethrough. The piercer carriage can include a resilient member that resides above or below the platform. In operation, the resilient member compresses and pushes against the piercer causing the piercer to travel down or up through the platform aperture to pierce at least one sealant associated with a respective dose container.

The dose container disk can have an open center portion and the (radially biasing) resilient member can be mounted aligned with the open center portion of the dose container disk and causes the piercer carriage travel radially outward and inward relative to an upwardly extending centerline of the open space so that the piercer is able to pierce sealants associated with different dose containers.

The inhaler can include a platform with an aperture extending therethrough. The piercer carriage can optionally include a substantially U-shaped flexible member attached to the platform. The substantially U-shaped flexible member can have two legs, a closed end and an opposing open end, oriented such that the legs of the U-shape reside one above the other above or below the dose container disk attached to the platform, with the open end of the "U" facing an outer perimeter of the dose container disk. The piercer can extend upwardly or downwardly between the legs of the U-shaped member proximate the open end thereof aligned with the platform aperture, whereby the piercer is configured to travel through the aperture to open a dose container thereunder or thereabove. Other spring configurations or resilient members can be used to facilitate the piercing action, including, for example, a leaf spring, a dome spring(s), spring washers, polymeric elastic members, and the like.

In some embodiments, the inhaler has an actuation member and associated shelf that can include a cam and gear teeth.

The inhaler may also include a gear train in the inhaler housing. The gear train can include a drive gear held by a platform of the piercer carriage, an idler gear in communication with the drive gear, and a clutch assembly gear in communication with the idler gear. The drive gear can engage the gear teeth of the actuation member shelf to rotate the drive gear, and the clutch assembly gear can be in communication with the gear teeth operably associated with the dose disk assembly. In operation, the drive gear rotates the idler gear, and which, in turn, when engaged with the clutch assembly gear, rotates the clutch assembly gear that rotates the dose container assembly to thereby index a dose container into an inhalation position in the inhaler.

Embodiments of the invention provide dose container assemblies that can define individual airway channels for one or more dose containers that align with an inhalation port and capture dry powder from a respective dose container(s) to define part of the inhalation path to the inhalation port for dispensing the dry powder to a user of the inhaler.

Other embodiments are directed to methods of operating an inhaler. The methods include: (a) providing a dose container ring having staggered concentric dose container apertures in an inner row and in an outer row sealed by upper and lower sealant layers over and under the apertures with dry powder in sealed dose container apertures; (b) rotating the dose container ring to present a respective dose container in a dispensing position in the inhaler; (c) radially advancing a piercing mechanism to align a piercer over a dose container in the outer row to open both sealant layers and release a first dose of dry powder from the aligned dose container (for inhalation delivery to a user); and subsequently (d) radially retracting the piercing mechanism to align the piercer over a dose container in the inner row to open both sealant layers and release a second dose of dry powder from the aligned dose container (for inhalation delivery to the user).

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE FIGURES

FIG. 2A is a top perspective view of a dose container assembly according to some embodiments of the present invention.

FIG. 2B is an exploded view of the assembly shown in FIG. 2A.

FIG. 2C is a partial cutaway view of airway channels aligned with two dose containers according to some embodiments of the present invention.

FIG. 6 is a greatly enlarged partial view of the dose container assembly shown in FIG. 2A according to embodiments of the present invention.

FIG. 10 is a partial exploded view of the device shown in FIG. 9A according to some embodiments of the present invention.

FIG. 11 is a top assembled view of the portion of the device shown in FIG. 10.

FIG. 12 is a side section view taken along lines 12-12 of FIG. 11, illustrating an outer ring actuation according to some embodiments of the present invention.

FIG. 17A is a greatly enlarged partial cutaway view of an inhaler according to some embodiments of the present invention.

FIGS. 17B-17D are greatly enlarged partial cutaway side perspective views of an inhaler with a biasing mechanism according to embodiments of the present invention.

FIG. 19A is an enlarged partial section view of an alternate piercing mechanism for the dose containers according to some embodiments of the present invention.

FIG. 19B is an enlarged partial section view of a piercing mechanism similar to that shown in FIG. 19A according to some embodiments of the present invention.

FIG. 19C is a partial front schematic view of a piercing mechanism with a fluted piercer according to some embodiments of the present invention.

FIG. 19D is an end view of the device shown in FIG. 19C.

FIG. 19E is a partial front schematic view of another fluted piercer configuration according to some embodiments of the present invention.

FIG. 19F is an end view of a fluted piercer with four lobes according to some embodiments of the present invention.

FIG. 20 is a flow chart of exemplary operations that can be used to operate an inhaler according to some embodiments of the present invention.

FIG. 22A is a partial cutaway top perspective view of a piercing mechanism with a radially biased piercing head engaging a dose container on an outer row according to embodiments of the present invention.

FIG. 22B is a partial cutaway top perspective view of the piercing mechanism shown in FIG. 22A illustrating the piercing mechanism engaging a dose container on an inner row according to some embodiments of the present invention.

FIGS. 23A and 23B are schematic illustrations of exemplary stops arranged on the dose container assembly and cooperating piercer carriage member to help radially align and position the piercer according to some embodiments of the present invention.

DESCRIPTION OF EMBODIMENTS OF THE INVENTION

Figure 1:
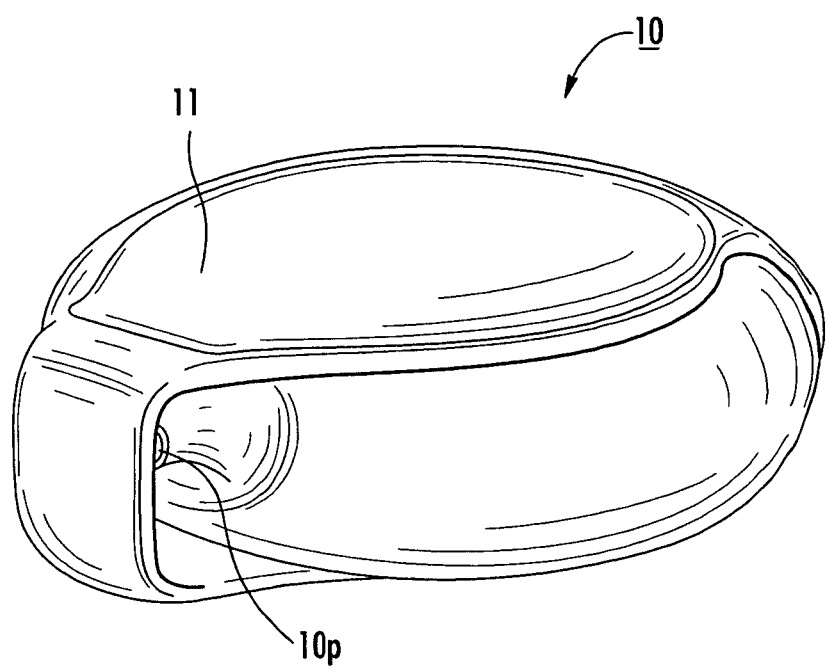
FIG. 1 is a front perspective view of an inhaler with a cover according to some embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise. Features described with respect to one figure or embodiment can be associated with another embodiment of figure although not specifically described or shown as such.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various regions, layers and/or sections, these regions, layers and/or sections should not be limited by these terms. These terms are only used to distinguish one component, region, layer or section from another component, region, layer or section. Thus, a first component, region, layer or section discussed below could be termed a second component, region, layer or section, and vice versa, without departing from the teachings of the present invention. Like numbers refer to like elements throughout.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

In the description of the present invention that follows, certain terms are employed to refer to the positional relationship of certain structures relative to other structures. As used herein, the term "front" or "forward" and derivatives thereof refer to the general or primary direction that the dry powder travels to be dispensed to a patient from a dry powder inhaler; this term is intended to be synonymous with the term "downstream," which is often used in manufacturing or material flow environments to indicate that certain material traveling or being acted upon is farther along in that process than other material. Conversely, the terms "rearward" and "upstream" and derivatives thereof refer to the direction opposite, respectively, the forward or downstream direction.

The term "deagglomeration" and its derivatives refer to processing dry powder in the inhaler airflow path to inhibit the dry powder from remaining or becoming agglomerated or cohesive during inspiration.

The inhalers and methods of the present invention may be particularly suitable for holding a partial or bolus dose or doses of one or more types of particulate dry powder substances that are formulated for in vivo inhalant dispersion (using an inhaler) to subjects, including, but not limited to, animal and, typically, human subjects. The inhalers can be used for nasal and/or oral (mouth) respiratory inhalation delivery, but are typically oral inhalers.

The terms "sealant", "sealant layer" and/or "sealant material" includes configurations that have at least one layer of at least one material and can be provided as a continuous layer that covers the entire upper surface and/or lower surface or may be provided as strips or pieces to cover portions of the device, e.g., to reside over at least a target one or more of the dose container apertures. Thus, terms "sealant" and "sealant layer" includes single and multiple layer materials, typically comprising at least one foil layer. The sealant or sealant layer can be a thin multi-layer laminated sealant material with elastomeric and foil materials. The sealant layer can be selected to provide drug stability as they may contact the dry powder in the respective dose containers.

The sealed dose containers can be configured to inhibit oxygen and moisture penetration to provide a sufficient shelf life.

The term "primary surface" refers to a surface that has a greater area than another surface and the primary surface can be substantially planar or may be otherwise configured. For example, a primary surface can include protrusions or recessions, such as where some blister configurations are used. Thus, a disk can have upper and lower primary surfaces and a minor surface (e.g., a wall with a thickness) that extends between and connects the two.

The dry powder substance may include one or more active pharmaceutical constituents as well as biocompatible additives that form the desired formulation or blend. As used herein, the term "dry powder" is used interchangeably with "dry powder formulation" and means that the dry powder can comprise one or a plurality of constituents or ingredients with one or a plurality of (average) particulate size ranges. The term "low-density" dry powder means dry powders having a density of about 0.8 g/cm$^3$ or less. In particular embodiments, the low-density powder may have a density of about 0.5 g/cm$^3$ or less. The dry powder may be a dry powder with cohesive or agglomeration tendencies.

The term "filling" means providing a bolus or sub-bolus metered amount of dry powder. Thus, the respective dose container is not required to be volumetrically full.

In any event, individual dispensable quantities of dry powder formulations can comprise a single ingredient or a plurality of ingredients, whether active or inactive. The inactive ingredients can include additives added to enhance flowability or to facilitate aerosolization delivery to the desired target. The dry powder drug formulations can include active particulate sizes that vary. The device may be particularly suitable for dry powder formulations having particulates which are in the range of between about 0.5-50 µm, typically in the range of between about 0.5 µm-20.0 µm, and more typically in the range of between about 0.5 µm-8.0 µm. The dry powder formulation can also include flow-enhancing ingredients, which typically have particulate sizes that may be larger than the active ingredient particulate sizes. In certain embodiments, the flow-enhancing ingredients can include excipients having particulate sizes on the order of about 50-100 µm. Examples of excipients include lactose and trehalose. Other types of excipients can also be employed, such as, but not limited to, sugars which are approved by the United States Food and Drug Administration ("FDA") as cryoprotectants (e.g., mannitol) or as solubility enhancers (e.g., cyclodextrine) or other generally recognized as safe ("GRAS") excipients.

"Active agent" or "active ingredient" as described herein includes an ingredient, agent, drug, compound, or composition of matter or mixture, which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized and/or systemic effect in a patient.

The active ingredient or agent that can be delivered includes antibiotics, antiviral agents, anepileptics, analgesics, anti-inflammatory agents and bronchodilators, and may be inorganic and/or organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable agents may be selected from, for example and without limitation, polysaccharides, steroids, hypnotics and sedatives, psychic energizers, tranquilizers, anticonvulsants, muscle relaxants, anti-Parkinson agents, analgesics, anti-inflammatories, muscle contractants, antimicrobials, antimalarials, hormonal agents including contraceptives, sympathomimetics, polypeptides and/or proteins (capable of eliciting physiological effects), diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines. Where the active agent is insulin, the term "insulin" includes natural extracted human insulin, recombinantly produced human insulin, insulin extracted from bovine and/or porcine and/or other sources, recombinantly produced porcine, bovine or other suitable donor/extraction insulin and mixtures of any of the above. The insulin may be neat (that is, in its substantially purified form), but may also include excipients as commercially formulated. Also included in the term "insulin" are insulin analogs where one or more of the amino acids of the naturally occurring or recombinantly produced insulin has been deleted or added.

It is to be understood that more than one active ingredient or agent may be incorporated into the aerosolized active agent formulation and that the use of the term "agent" or "ingredient" in no way excludes the use of two or more such agents. Indeed, some embodiments of the present invention contemplate administering combination drugs that may be mixed in situ.

Examples of diseases, conditions or disorders that may be treated according to embodiments of the invention include, but are not limited to, asthma, COPD (chronic obstructive pulmonary disease), viral or bacterial infections, influenza, allergies, cystic fibrosis, and other respiratory ailments as well as diabetes and other insulin resistance disorders. The dry powder inhalation may be used to deliver locally-acting agents such as antimicrobials, protease inhibitors, and nucleic acids/oligionucleotides as well as systemic agents such as peptides like leuprolide and proteins such as insulin. For example, inhaler-based delivery of antimicrobial agents such as antitubercular compounds, proteins such as insulin for diabetes therapy or other insulin-resistance related disorders, peptides such as leuprolide acetate for treatment of prostate cancer and/or endometriosis and nucleic acids or ogligonucleotides for cystic fibrosis gene therapy may be performed. See e.g. Wolff et al., *Generation of Aerosolized Drugs*, J. Aerosol. Med. pp. 89-106 (1994). See also U.S. Patent Application Publication No. 20010053761, entitled *Method for Administering ASPB28-Human Insulin* and U.S. Patent Application Publication No. 20010007853, entitled *Method for Administering Monomeric Insulin Analogs*, the contents of which are hereby incorporated by reference as if recited in full herein.

Typical dose amounts of the unitized dry powder mixture dispersed in the inhalers may vary depending on the patient size, the systemic target, and the particular drug(s). The dose amounts and type of drug held by a dose container system may vary per dose container or may be the same. In some embodiments, the dry powder dose amounts can be about 100 mg or less, typically less than 50 mg, and more typically between about 0.1 mg to about 30 mg.

In some embodiments, such as for pulmonary conditions (i.e., asthma or COPD), the dry powder can be provided as about 5 mg total weight (the dose amount may be blended to provide this weight). A conventional exemplary dry powder dose amount for an average adult is less than about 50 mg, typically between about 10-30 mg and for an average adolescent pediatric subject is typically from about 5-10 mg. A typical dose concentration may be between about 1-5%. Exemplary dry powder drugs include, but are not limited to, albuterol, fluticasone, beclamethasone, cromolyn, terbutaline, fenoterol, β-agonists (including long-acting β-agonists), salmeterol, formoterol, cortico-steroids and glucocorticoids.

In certain embodiments, the administered bolus or dose can be formulated with an increase in concentration (an increased percentage of active constituents) over conventional blends. Further, the dry powder formulations may be configured as a smaller administrable dose compared to the conventional 10-25 mg doses. For example, each administrable dry powder dose may be on the order of less than about 60-70% of that of conventional doses. In certain particular embodiments, using the dispersal systems provided by certain embodiments of the DPI configurations of the instant invention, the adult dose may be reduced to under about 15 mg, such as between about 10 µg-10 mg, and more typically between about 50 µg-10 mg. The active constituent(s) concentration may be between about 5-10%. In other embodiments, active constituent concentrations can be in the range of between about 10-20%, 20-25%, or even larger. In particular embodiments, such as for nasal inhalation, target dose amounts may be between about 12-100 µg.

In certain particular embodiments, during inhalation, the dry powder in a particular drug compartment or blister may be formulated in high concentrations of an active pharmaceutical constituent(s) substantially without additives (such as excipients). As used herein, "substantially without additives" means that the dry powder is in a substantially pure active formulation with only minimal amounts of other non-biopharmacological active ingredients. The term "minimal amounts" means that the non-active ingredients may be present, but are present in greatly reduced amounts, relative to the active ingredient(s), such that they comprise less than about 10%, and preferably less than about 5%, of the dispensed dry powder formulation, and, in certain embodiments, the non-active ingredients are present in only trace amounts.

In some embodiments, the unit dose amount of dry powder held in a respective drug compartment or dose container is less than about 10 mg, typically about 5 mg of blended drug and lactose or other additive (e.g., 5 mg LAC), for treating pulmonary conditions such as asthma. Insulin may be provided in quantities of about 4 mg or less, typically about 3.6 mg of pure insulin. The dry powder may be inserted into a dose container/drug compartment in a "compressed" or partially compressed manner or may be provided as free flowing particulates.

Some embodiments of the invention are directed to inhalers that can deliver multiple different drugs for combination delivery. Thus, for example, in some embodiments, some or all of the dose containers may include two different drugs or different dose containers may contain different drugs configured for dispensing substantially concurrently.

The inhalers can be configured to provide any suitable number of doses, typically between about 30-120 doses, and more typically between about 30-60 doses. The inhalers can deliver one drug or a combination of drugs. In some embodiments, the inhalers can provide between about 30-60 doses of two different drugs (in the same or different unit amounts), for a total of between about 60-120 individual unit doses, respectively. The inhaler can provide between a 30 day to a 60 day (or even greater) supply of medicine. In some embodiments, the inhalers can be configured to hold about 60 doses of the same drug or drug combination, in the same or different unit amounts, which can be a 30 day supply (for a twice per day dosing) or a 60 day supply for single daily treatments.

The dose container assembly and inhaler may be particularly suitable for dispensing medicament for the treatment of respiratory disorders. Appropriate medicaments may be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (−)-4-amino-3,5-dichloro-α-[[6-[2-(2-pyridinyl)ethoxy]hexyl]methyl]benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. It will be clear to a person of skill in the art that, where appropriate, the medicaments may be used in the form of salts, (e.g., as alkali metal or amine salts or as acid addition salts) or as esters (e.g., lower alkyl esters) or as solvates (e.g., hydrates) to optimize the activity and/or stability of the medicament.

Some particular embodiments of the dose container assembly and/or inhaler include medicaments that are selected from the group consisting of: albuterol, salmeterol, fluticasone propionate and beclometasone dipropionate and salts or solvates thereof, e.g., the sulphate of albuterol and the xinafoate of salmeterol. Medicaments can also be delivered in combinations. Examples of particular formulations containing combinations of active ingredients include those that contain salbutamol (e.g., as the free base or the sulphate salt) or salmeterol (e.g., as the xinafoate salt) in combination with an anti-inflammatory steroid such as a beclomethasone ester (e.g., the dipropionate) or a fluticasone ester (e.g., the propionate).

Turning now to the figures, FIG. 1 illustrates an example of a multi-dose inhaler 10 with a cover 11 and inhalation port 10p. However, this inhaler configuration is shown merely for completeness and embodiments of the invention are not limited to this inhaler configuration as other form factors, covers and inhalation port configurations may be used.

FIG. 2A illustrates a dose container assembly 20 with a dose container ring or disk 30 having a plurality of dose containers 30c. As shown in FIG. 2B, in some embodiments, the dose ring or disk 30 can include a plurality of circumferentially spaced apart through apertures 30a that forms a portion of the dose containers 30c.

Although the dose container disk 30 is described primarily herein as used with one or more airway disks 40, 50, it is contemplated that the dose container disk 30 can be used alone or with other airway channels and embodiments are not limited to use with airway disks.

Figure 3A:
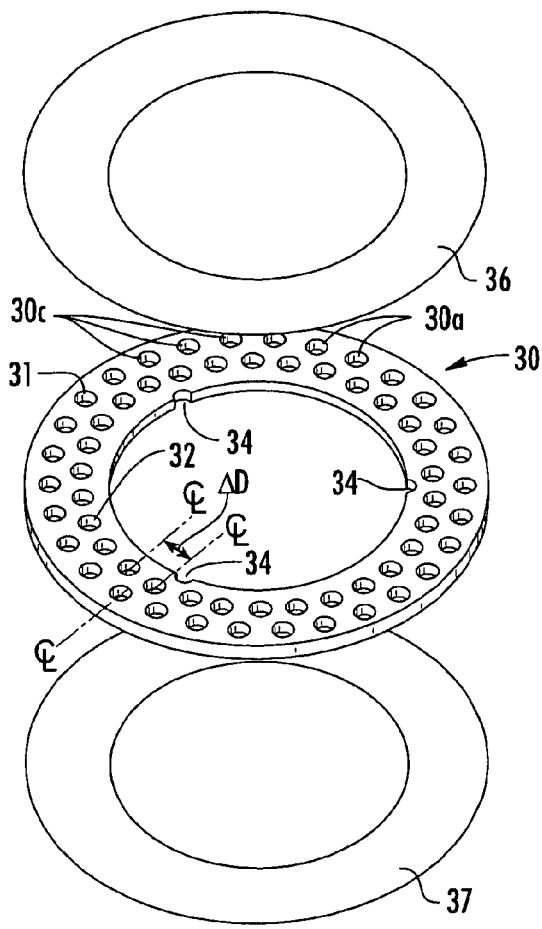
FIG. 3A is a top perspective view of a dose container ring according to some embodiments of the present invention.
Figure 3B:
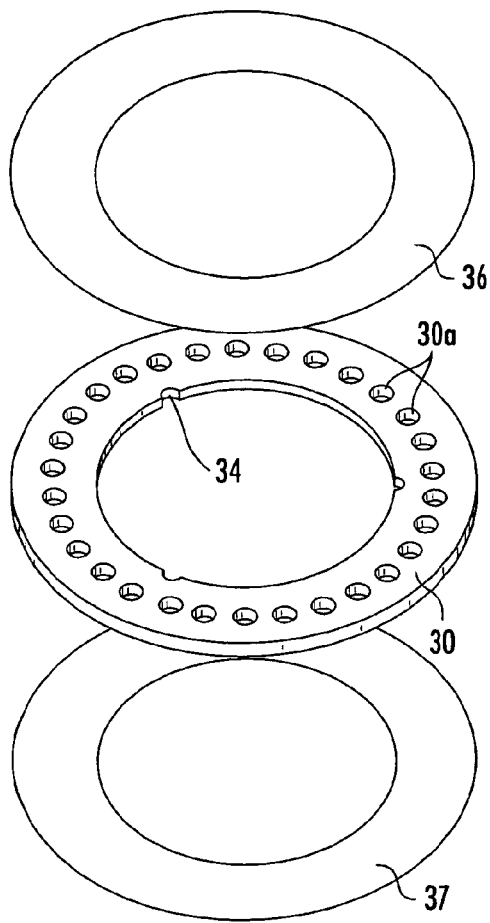
FIG. 3B is a top perspective view of a dose container ring according to some other embodiments of the present invention.

FIGS. 3A and 3B illustrate that the dose container disk 30 can include an upper sealant 36 and a lower sealant 37, shown as annular flat rings. The sealant layers 36, 37 can seal the top and bottom surfaces of the dose disk 30 with the dry powder held therebetween. The sealant layers 36, 37 can have the same or different material(s) and may include foil, polymer(s) and/or elastomer(s), or other suitable material or combinations of materials, including laminates. Typically, the sealant layers 36, 37 are thin flexible sealant layers comprising foil. FIGS. 3A and 3B illustrate that the dose containers 30c are provided as a plurality of circumferentially spaced apart dose containers in one or more rows (typically concentric and/or optionally with staggered or offset radial centerline dose containers).

The sealant layers 36, 37 (where used) may be provided as a substantially continuous ring as shown in FIGS. 3A and 3B or may be attached to the dose container disk 30 as individual strips or spots of sealant that can be placed over and under the apertures 30a. In other embodiments, sealant layers may be provided on only one primary surface of the dose disk 30, and the apertures 30a may be closed on one side rather than have through apertures (not shown). In yet other embodiments, the dose disk 30 can have a blister configuration 130 (FIG. 17A).

Turning again to FIGS. 2A and 2B, in some embodiments, the dose disk 30 is held in a dose container assembly 20 that includes a lower airway disk 40 and an upper airway disk 50. In other embodiments, the dose container assembly 20 can include the dose container disk 30 and only one of the lower airway disk 40 or the upper airway disk 50. In such a configuration, another type of airway can be used for the other side of the disk 30, such as, but not limited to, a fixed or "global" upper or lower airway can be used with the individual airways provided by either an upper or lower airway disk 50, 40. Also, it is contemplated that the upper and lower airway disks 50, 40 described herein can be reversed for normal operation (or inadvertently for atypical operation) so that the lower airway disk is the upper airway disk and the upper airway disk is the lower airway disk.

As shown in FIGS. 2A and 2B, the lower and upper airway disks 40, 50, respectively, include a plurality of circumferentially spaced apart airway channels 41, 51, respectively. Typically, the disks 40, 50 include one channel 41, 51 for one dose container 30c. However, in other embodiments, as shown, for example, in FIG. 2C, a respective airway channel 51, 41 from one or both of the disks 50', 40' can be in communication with two different dose containers 30c. This configuration will allow for (simultaneous) combination delivery of dry powder from two containers in a respective airway channel pair (or single) or can allow one dose container $30c_1$ to release dry powder to the airway channel 41 and/or 51, then be used again later for the other dose container $30c_2$. Thus, embodiments of the invention allow for some or all airway channels 41, 51 to be used once or twice. Also, while embodiments of the invention are illustrated as releasing only a dose from a single dose container 30c during one delivery, other embodiments allow the inhalers to dispense a combination drug so that two or more dose containers 30c may use a respective airway channel 41, 51 for delivery.

In some embodiments, the airway channels 41, 51 can define airways that are not able to release dry powder residing in a respective airway channel to a user once the inhaler is indexed again to another position so that the outer ring of dose containers are aligned with airway disks. The channels can be configured to have "sink traps" to inhibit spillage according to some embodiments of the present invention to provide overdose protection (unless the dual use configuration is used whereby only a single other dose may be released using that airway channel(s) as noted above).

Where two airway disks are used, e.g., both the lower and upper disks 40, 50, the inhaler device 10 can be configured to operate even when inverted and have the same overdose protection feature. Spillage of dry powder from the inhaler 10 as the dose container 30c is opened can be influenced by gravity. For example, for a conventional obround or elliptical mouthpiece shape, there are two primary device orientations (right-side-up and upside-down), embodiments of the invention allow for operation of the inhaler device in both orientations. In the embodiment shown, for example, in FIG. 2A, this can be accomplished by having an individual airway section for a respective dose container 30c (or dose containers where combination drug delivery is desired) both above and below the target corresponding dose container(s) 30c.

FIGS. 2A and 3A illustrate that the dose container disk 30 can include 60 dose containers 30c while FIG. 3B illustrates that the dose container disk 30 can include 30 dose containers 30c. Greater or lesser numbers of dose containers may be used.

FIGS. 2A, 3A and 3B also illustrate that the dose container disk 30 can include at least one indexing notch 34, shown as a plurality of circumferentially spaced apart indexing notches 34. To assemble the assembly 20, a tab on one of the airway disks 40, 50, typically the lower disk 40, includes a radially extending tab 45 (FIGS. 4A, 6) that aligns with and engages one of those notches 34 to position the channels 41, 51 in alignment with the dose containers 30c. Other alignment means may be used including the reverse of the notch and tab configuration described (e.g., the airway disk can have the notch and the dose container disk can have the tab).

As shown in FIGS. 2B, 3A and 3B, the dose containers 30c may be arranged so that they are circumferentially spaced apart in one or more rows. As shown in FIG. 3A, the dose containers 30c are arranged in staggered concentric rows, a front row 31 at a first radius from a center of the disk and a back row 32 at a second different radius. The dose containers 30c can be arranged so that centerlines of the dose containers 30c of the back row are circumferentially offset from the radial centerlines of the dose containers 30c in the front row by a distance "D/2" with the dose containers on each row separated by a distance "D" as shown in FIG. 3A. The offset distance can correspond to about 6 degrees of rotation of the disk. The dose container disk 30 can be a molded polymer, copolymer or blends and derivatives thereof, or may comprise metal, or combinations thereof, or other materials that are capable of providing sufficient moisture resistance.

Figure 3C:
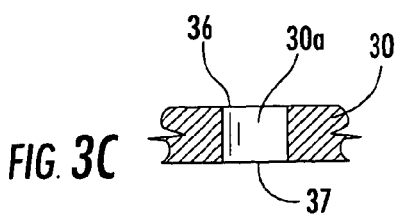
FIG. 3C is a partial cutaway view of a single dose container according to some embodiments of the present invention.
Figure 3D:
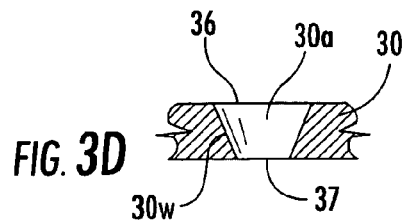
FIG. 3D is a partial cutaway view of a single dose container according to some embodiments of the present invention.

The dose container disk 30 can have an outer diameter of between about 50-100 mm, typically about 65 mm and a thickness of between about 2-5 mm, typically about 3 mm. The disk 30 can comprise a cyclic olefin (COC) copolymer. The apertures 30a can have a diameter of between about 2-5 mm, typically about 3 mm and the sidewalls 30w of the dose containers 30c may have an angle or draft of about 1-3 degrees per side, typically about 1.5 degrees, as shown in FIG. 3D, to facilitate removal from a mold (where a molding process is used to form the disk 30). The dose container 30 is configured to be able to protect the powder from moisture ingress, while providing a desired number of doses in a compact overall inhaler size. The individual dose apertures 30a are spaced apart from each other to allow sufficient seal area and material thickness for moisture protection of the powder.

As discussed above, FIGS. 3A, 3B and 3C illustrate that the dose containers 30c may be defined by apertures 30a sealed by sealant layers 36, 37 over and under the apertures 30a. The sealant can include foil, a polymer and/or elastomer, or other suitable materials or combinations of materials, including laminates. In a dry powder medicament inhaler 10, the drug powder is stored in a closed, moisture-resistant space provided by the dose containers 30c. The sealant layers 36, 37 (where used) may be provided as a substantially continuous ring or may be attached to the dose container disk 30 as individual strips or spots of sealant can be placed over and under the apertures 30a. In other embodiments, sealant is only provided on one primary surface of the dose disk, and the apertures 30a may be closed on one side rather than through apertures (not shown). In yet other embodiments, the dose disk 30 can have a blister configuration 130 (FIG. 17A).

Particular embodiments of the invention provide a dose container assembly 20 that can provide a suitable seal and facilitate attachment of the airway disks 40, 50 to the dose ring or disk 30. In some embodiments, the dose container disk 30 contains sealants 36, 37 which may be a continuous layer over the upper and lower (primary) surfaces of the dose disk 30 and the upper and lower airway disks 50, 40 can contact the respective sealant and abut the dose disk to allow for a tight fit. The exemplary attachment features shown in FIGS. 2A and 6 can reduce air leakage by allowing a close fit of the airway disks 40, 50 to the dose ring 30. The disks 40, 50 can sandwich the dose ring 30 and the dose ring can act as the "stop" to set the depth of engagement of the assembly features on the airway disks 40, 50. Embodiments of the invention provide a feature to index the airway disks 40, 50 relative to the dose ring 30, and some simple frictional engagement members, such as, but not limited to, "crush ribs", on one or both of the airway disks 40, 50 to secure their attachment to each other as will be discussed further below.

Figure 4A:
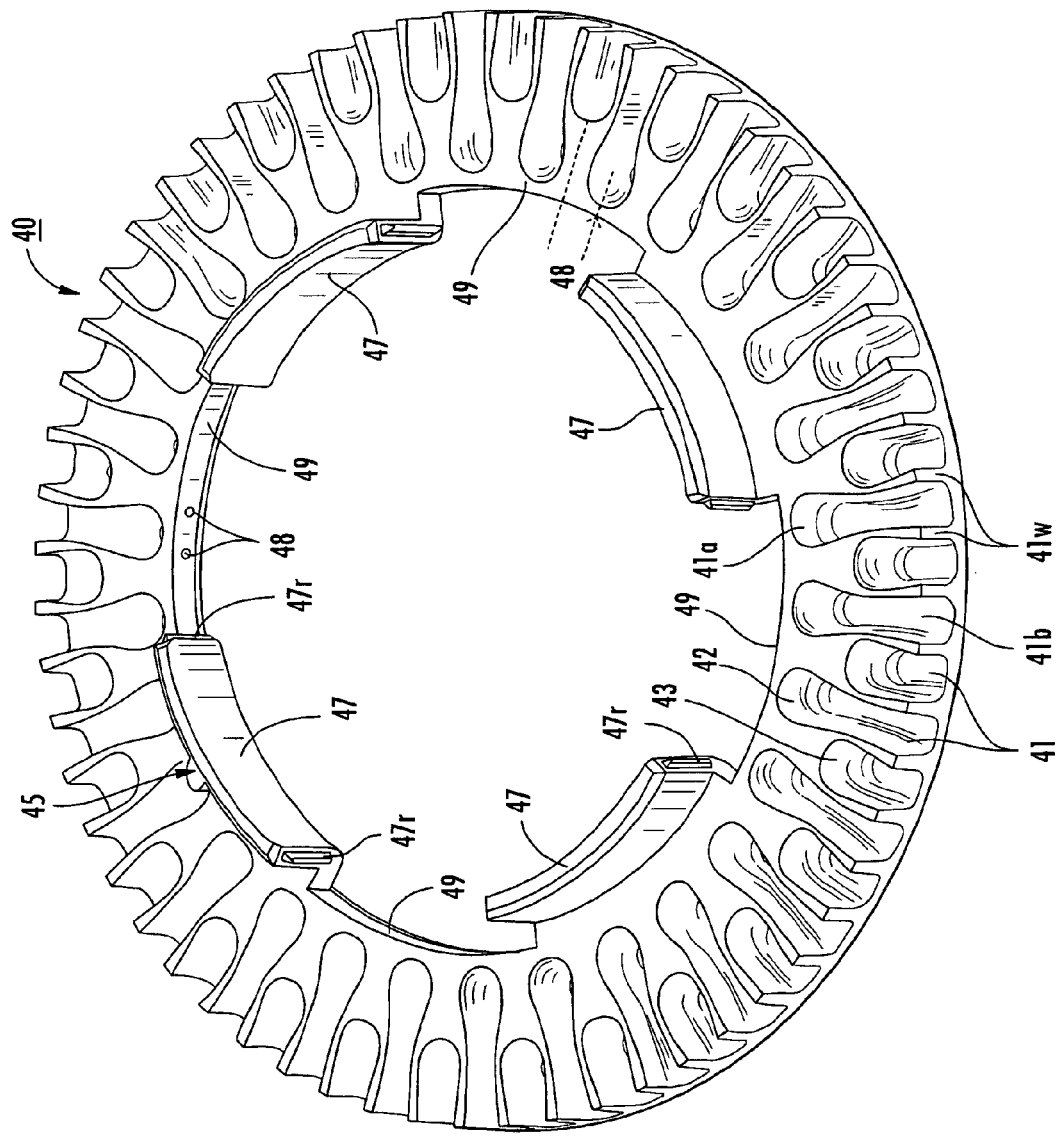
FIG. 4A is a greatly enlarged top perspective view of a lower airway disk according to some embodiments of the present invention.

FIG. 4A illustrates an example of a lower airway disk 40. As shown, the disk 40 defines a plurality of circumferentially spaced apart channels 41. For the staggered concentric dose container configuration, the disk 40 can include alternating long and short airway channels 42, 43, respectively. Each channel 41 includes opposing end portions 41a, 41b, one (substantially or entirely) closed end portion 41a typically positioned adjacent the dose container 30c and one open end portion 41b. The open end portion end portion 41b can merge into and/or is positioned adjacent the exit port 10p and/or mouthpiece 10m (FIGS. 7A-7C) and/or a make-up air port or channel. The intake and flow can be in either direction and the open end 41b can be configured to face either the inner or outer perimeter of the disk 40 (e.g., be either positioned radially innermost or radially outermost on the disk 40). The channels 41 include upwardly extending sidewalls 41w with adjacent pairs of the long and short channels sharing one of the sidewalls 41w. Optionally, as shown by the broken line with respect to feature 48 in FIG. 4A, the channels 41 can include a small bleed hole 48 that allows air to enter but is sized to inhibit dry powder from exiting therefrom.

FIG. 4A also illustrates that the disk 40 can include circumferentially spaced apart upwardly extending tabs 47. One of which includes the radially extending tab 45 discussed above. The disk 40 can also include circumferentially extending recesses which align with tabs on the upper airway disk 50 to sandwich the dose disk therebetween. The tabs 47 can include crush ribs 47r that matably engages tabs 57 on the upper airway disk to hold the three piece assembly 20 with sufficient force without requiring and additional attachment means. FIG. 4A illustrates four circumferentially spaced apart tabs 47 while FIG. 4B illustrates three.

Figure 4B:
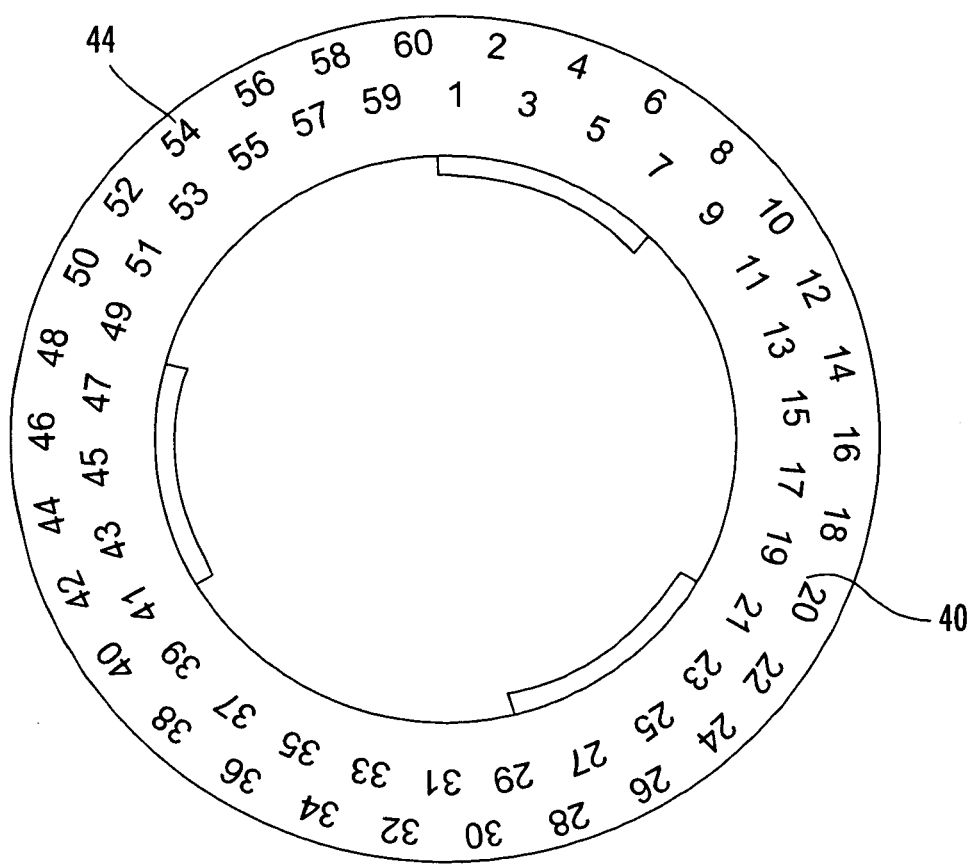
FIG. 4B is a bottom view of the lower airway disk illustrating optional dose indicia and a different number of tabs according to some embodiments of the present invention.

FIG. 4B illustrates that the disk 40 can also include dose indicia 44 so that a user can visually note what dose is being dispensed or a number of doses left in the inhaler. The dose indicia 44 can align with a dose reading aperture in the inhaler housing so that a user can visually assess the dose indicia/ information that is visible to a user when a respective dose is indexed or is next to be indexed, to the dispensing position. Dose indicia 44 may also or alternatively be placed on the upper disk 50 and aligned with a dose reading aperture (not shown), or on both disks (also not shown). FIG. 4B illustrates that indicia may be placed along the outer perimeter edge of the lower surface of the lower disk 40, and numbered sequentially 1-60, but other patterns may be used, depending on the opening sequence (and the number of doses on the disk). That is, this numbering may be appropriate where the inhaler is configured to open a dose container in one row, then open an adjacent dose container in the other row (e.g., inner to outer ring or outer to inner ring of dose containers), and repeating this sequence serially, where two rows of dose containers are used. However, other embodiments may open all the inner dose containers or all the outer dose containers, then open the dose containers in the other row or use a different alternating pattern of opening the dose containers on the inner and outer rows, and the dose numbering indicia on the disk 40 and/or 50 can be presented accordingly.

Figure 5A:
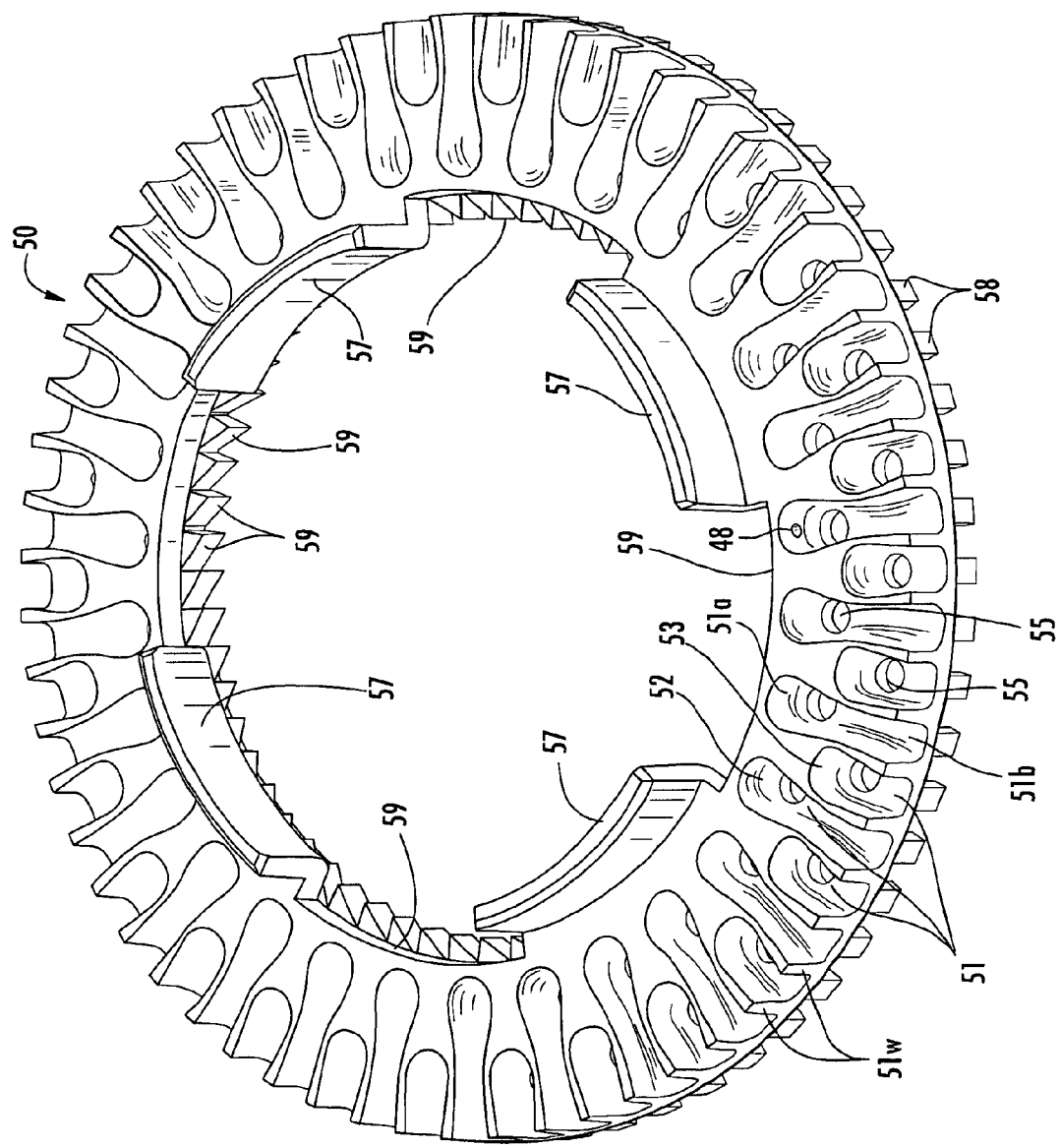
FIG. 5A is a greatly enlarged top perspective view of an upper airway disk according to some embodiments of the present invention.

FIG. 5A illustrates an example of an upper airway disk 50. In this embodiment, the upper airway disk 50 is shown inverted from its normal use position (and inverted relative to the orientation shown in FIG. 2A). As shown, the disk 50 defines a plurality of circumferentially spaced apart channels 51. For the staggered concentric dose container configuration, the disk 50 can include alternating long and short airway channels 52, 53, respectively. Each channel 51 includes opposing end portions 51a, 51b, the close or substantially closed portion 51a is typically positioned adjacent the dose container 30c. The intake and flow can be in either direction and the open end 51b can be configured to face either the inner or outer perimeter of the disk 50 (e.g., be either positioned radially innermost or radially outermost). The other (open) end portion 51b merges into and/or is positioned adjacent the exit port 10p and/or mouthpiece 10m and/or make-up air port or channel. The channels 51 include downwardly extending sidewalls 51w with adjacent pairs of the long and short channels sharing one of the sidewalls 51w. Optionally, as shown by the broken line with respect to feature 48 in FIG. 5A, the channels 51 can include a small bleed hole 48 that allows air to enter but is sized to inhibit dry powder from exiting therefrom.

As also shown in FIG. 5A, each channel 51 can include an aperture 55 that is configured to reside over a respective dose container 30c with the upper sealant layer 36 of the dose container 30c residing under the aperture 55. The apertures 55 allow a piercing (e.g., slicing or puncturing) mechanism to extend through the aperture and open the sealant layers 36, 37 (FIG. 3C). As shown in FIG. 5A, the upper disk 50 can also include one or more of indexing ribs 58 and/or inner perimeter gear teeth 59 or other features that can index the disk within the inhaler to rotate the disk to provide the different dose containers 30c to a dispensing position and/or position a piercing mechanism over the target dose container for dispensing to open the dose container 30c. The gear teeth may also or alternately be on the dose disk 30 and/or lower airway disk 40 (where used). In other embodiments, one or both of these rotating and positioning mechanisms (or different features) can be provided on the lower disk 40 (where used) or the dose disk 30 (not shown).

FIGS. 2A and 6 illustrate the dose container assembly 20 integrally attached together. FIGS. 2B, 4A, and 5A illustrate the exemplary disk components, 30, 40, 50. The tabs 57 of the disk 50 fit into spaces 49 of the disk 40 and the tabs 47 of the disk 40 fit into spaces 59 of the disk 50 with the crush ribs 47r firmly abutting the outer edges of tabs 57 to frictionally engage the components together with the dose container disk 30 sandwiched therebetween with a flush fit via a relatively easy "press-fit" assembly method. The dose container disk 30 is aligned with the upper and lower airway disks via the (radially outward extending) tab 45 that engages one of the alignment notches 34 of the dose container disk or ring 30 as discussed above. However, other alignment features or indicia may be used as well as other attachment configurations.

Figure 5B:
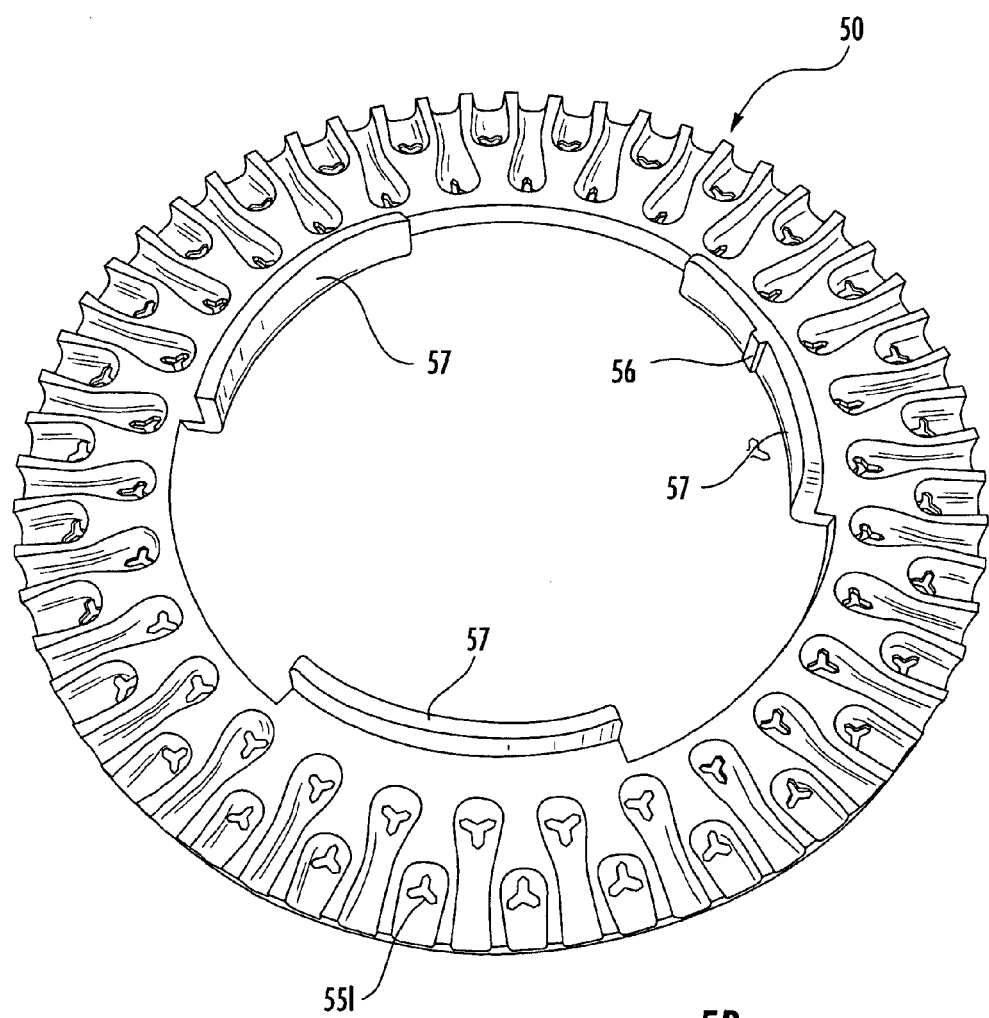
FIG. 5B is a greatly enlarged perspective view of an upper airway disk according to other embodiments of the present invention.

FIG. 5B illustrates that the disk 50 can include three tabs 57 instead of four as shown in FIG. 5A (the lower airway disk 40 can also include three tabs instead of four in this embodiment, see FIG. 4B). One of the tabs 57 can have a vertically extending orientation rib 56, shown on an inner perimeter surface of the tab 57. The orientation rib 56 is on the upper disk 50 cooperates with a piercing frame associated with the piercing mechanism fixed in the inhaler housing so that the orientation rib 56 aligns to the frame to set a correct initial position according to dose number (e.g., 1) and prevents indexing past the number of doses in the disk assembly 20. Stated differently, the orientation rib 56 cooperates with the inhaler housing to set an initial position of the disk assembly 20 and also stops the disk assembly from rotating around more than once.

Figure 18A:
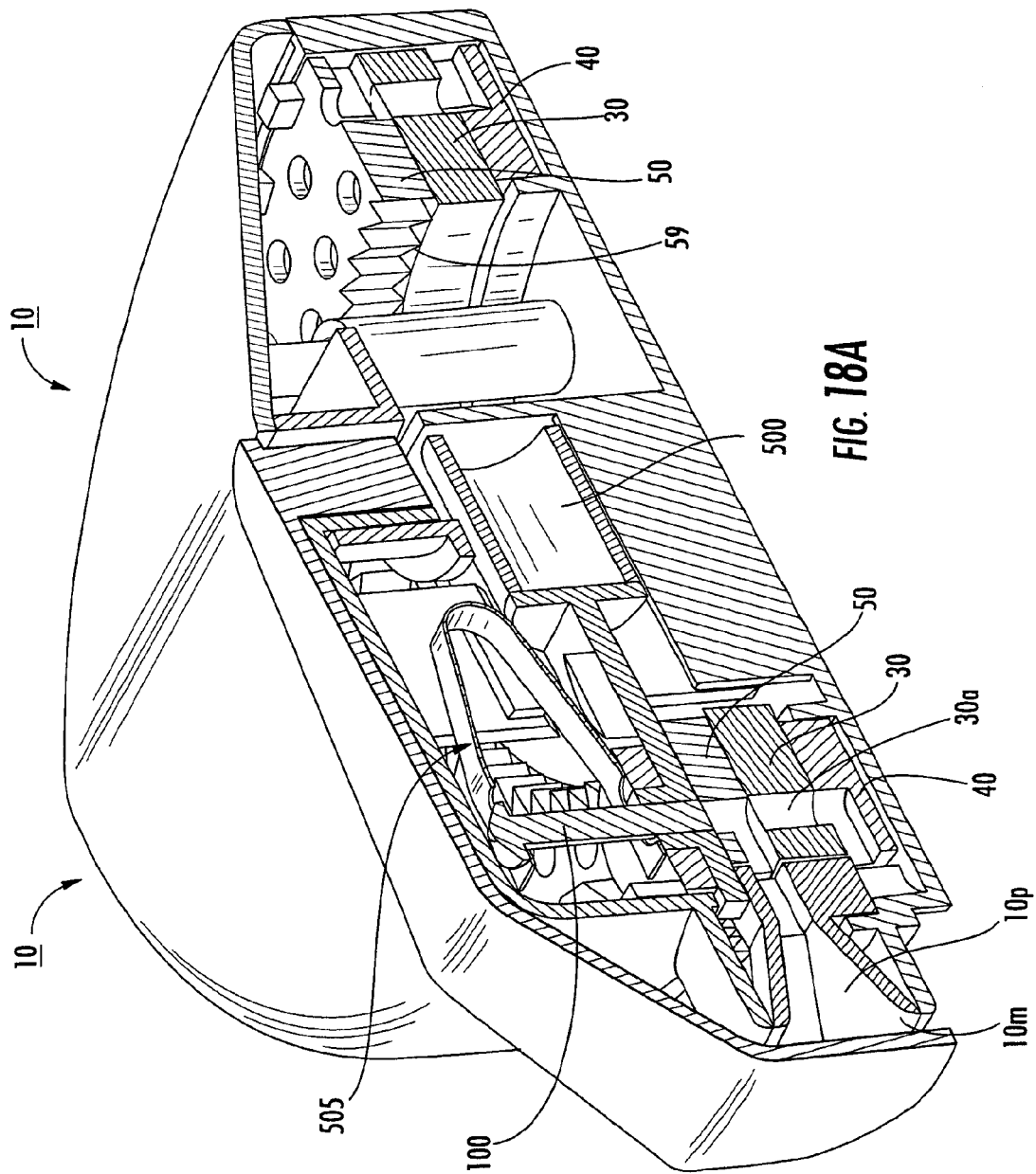
FIG. 18A is a greatly enlarged partial cutaway view of an inhaler according to some embodiments of the present invention.

FIG. 5B also illustrates that the apertures 55 can be configured with a geometry that corresponds to the shape of the piercer 100. The apertures 55 can be configured to closely surround the piercer 100 (FIG. 18A). The piercer 100 can be a fluted piercer. As shown, the aperture 55 has a plurality of lobes 55l, typically three or four lobes, to snugly matably receive a correspondingly shaped three or four lobe (fluted) piercer 111 (FIGS. 19C/19D). The lobes 55l can be in a different orientation in the inner row versus the outer row, e.g., rotated 180 degrees.

The upper and lower airway disks 50, 40 (where both are used) can be attached to the dose container disk 30 so as to reduce any gaps in the airway path defined thereby. In other embodiments, the upper and lower airway disks 50, 40 can attach to each other and hold the disk 30 therebetween. The disk 30 can be a stop for attachment features on the airway disks 40, 50. The disk 30 with the sealants 36, 37 can have substantially planar upper and lower primary surfaces without requiring any attachment features. The lower portion of the upper airway disk 50 and the upper portion of the lower airway disk 40 can snugly reside directly against the respective opposing primary surfaces of the dose container disk 30 so that the attachment features/components are only on the upper and lower disks 50, 40 allowing for a snug and sufficiently air-tight interface between the disks 30, 40, 50 without gaps created by tolerances in other build configurations. The press-fit attachment without use of adhesives while providing for the substantially air-tight interface can be advantageous and cost-effective. However, as noted above, other attachment configurations may be used, including, for example, ultrasonic welding, adhesive, laser weld, other friction fit and/or matable configurations, the use of seals (O-rings, gaskets and the like) between the connection regions of the walls of the airway channels facing the dose container 30c and the sealant layers 36, 37 over and/or under the dose containers 30c of the disk, including combinations thereof, and the like.

Figure 7A:
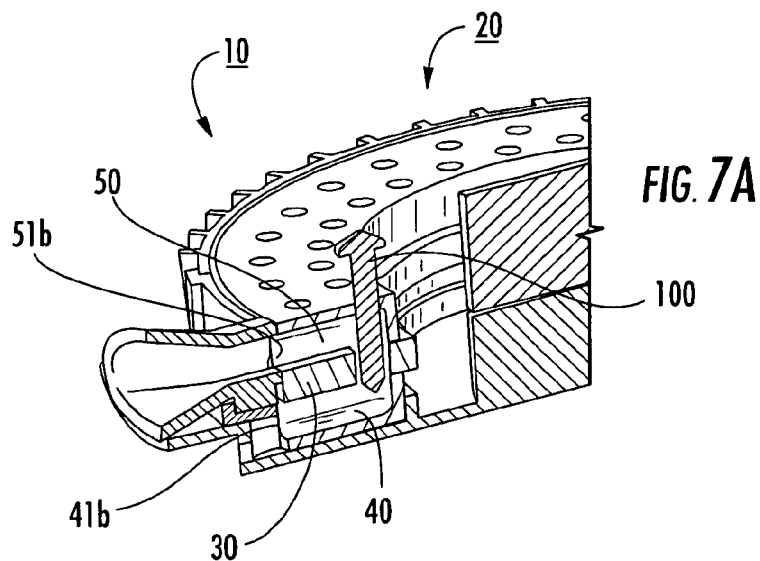
FIGS. 7A-7C are partial cutaway views of a dose container assembly in an inhaler cooperating with a piercing mechanism having a three-stage operation sequence according to some embodiments of the present invention.
Figure 7B:
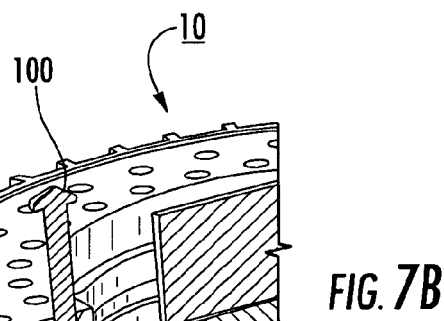
Figure 7C:
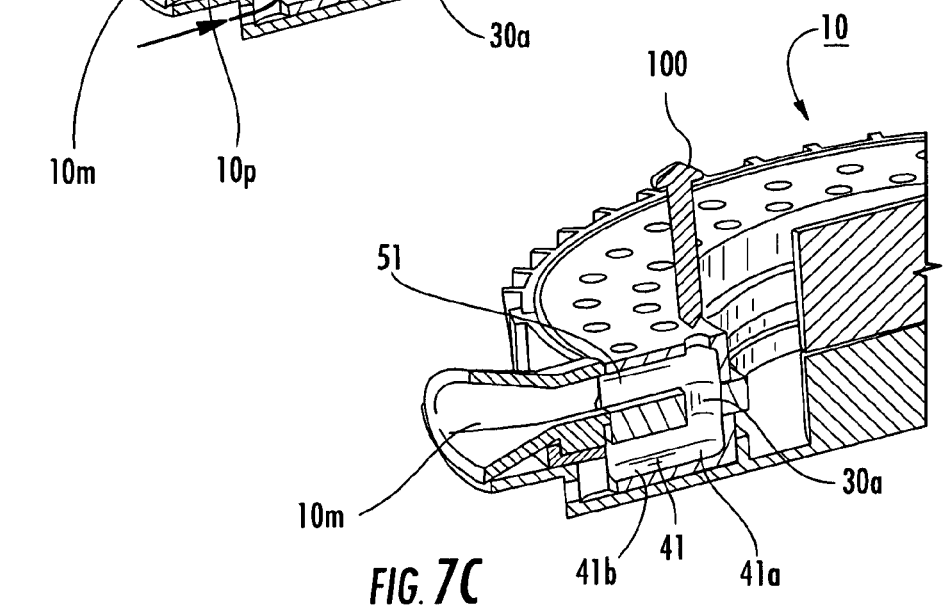

As shown in FIGS. 7A-7C, in operation, pairs of upper and lower aligned channels 41, 51 can reside over and under a respective dose container 30c and are in fluid communication via the opened dose container 30c and aperture 30a. That is, as shown in FIG. 7A, a piercing mechanism 100 advances to pierce the upper and lower sealant layers 36, 37, respectively (FIG. 3C). The piercing mechanism 100 can be configured to extend and remain in the lower airway channel or may (partially or fully) retract before the dispensing after opening the lower sealant. Also, although shown as extending down to pierce the sealant layers, the piercing mechanism can be configured to extend upward from the bottom. Either way, the piercing mechanism 100 can be configured to occlude the aperture 55 in the upper (or lower disk).

As shown in FIG. 7B, the piercing mechanism 100 can then partially or fully retract, or stay extended in the lower (or upper) airway channel, depending on the configuration of the mechanism, but is typically configured to plug and/or cooperate with a member that can plug the aperture 55 of the upper disk 50 or lower disk 40 (if piercing from the bottom) or otherwise occlude this passage 55 so that the piercing mechanism 100 and/or cooperating member substantially blocks, occludes (and/or seals) the aperture/opening 55 (FIGS. 2A, 5A). In this way, if the inhaler is inverted, powder is prevented from spilling out of the channel 51 because of the blockage provided by the piercing mechanism 100. The airflow path 10f may be any direction from above to below the dose container 30c or vice versa or from the inner perimeter to the outer or vice versa, shown for example only in FIG. 7B by the arrow to allow air to flow through the bottom channel up through the aperture 30a and out the top channel 51 to the mouthpiece 10m. It is also noted that the exit or open end portion of the channel 41b, 51b may face the inner perimeter rather than the outer perimeter of the disc assembly 20 as shown in FIGS. 7A-7C (see, e.g., FIG. 17A).

After dispensing, the piercing mechanism 100 is fully retracted as shown in FIG. 7C and the dose container assembly 20 can be rotated to a dispensing position and/or the piercing mechanism 100 can be activated to open a different dose container 30c. In operation, the dose container assembly 20 can be radially pushed outward to seal or provide a snug exit path for the airway channel 41 and/or 51 against the mouthpiece 10m.

FIG. 17A illustrates that a compliant seal 129, such as an O-ring may be used to provide a sufficiently air-tight path between the airflow exit path 10/(or short path 10s and/or mouthpiece 10m) and the disk assembly 20. Other airpath seal or closure configurations may be used.

FIGS. 17B-17E illustrate an embodiment of the inhaler 10 that can bias the disk assembly 20 toward the mouthpiece 10m using a lever assembly 80 that can facilitate an accurate, repeatable position of the disk assembly 20 for piercing, as well as control air leakage at the mouthpiece joint 10j. With regard to air leakage, embodiments of the inhaler provide a tight connection that is temporally synchronized with the time of inhalation, while at other times, e.g., during indexing of the disk assembly 20, the inhaler can allow a looser fit which facilitates rotation of the disk assembly 20 in the inhaler 10. In this embodiment, the mouthpiece 10m resides on the outer perimeter of the disk assembly 20 with the exit ports of the disk assembly 20 also residing on the outer perimeter of the disk assembly.

Figure 17B:
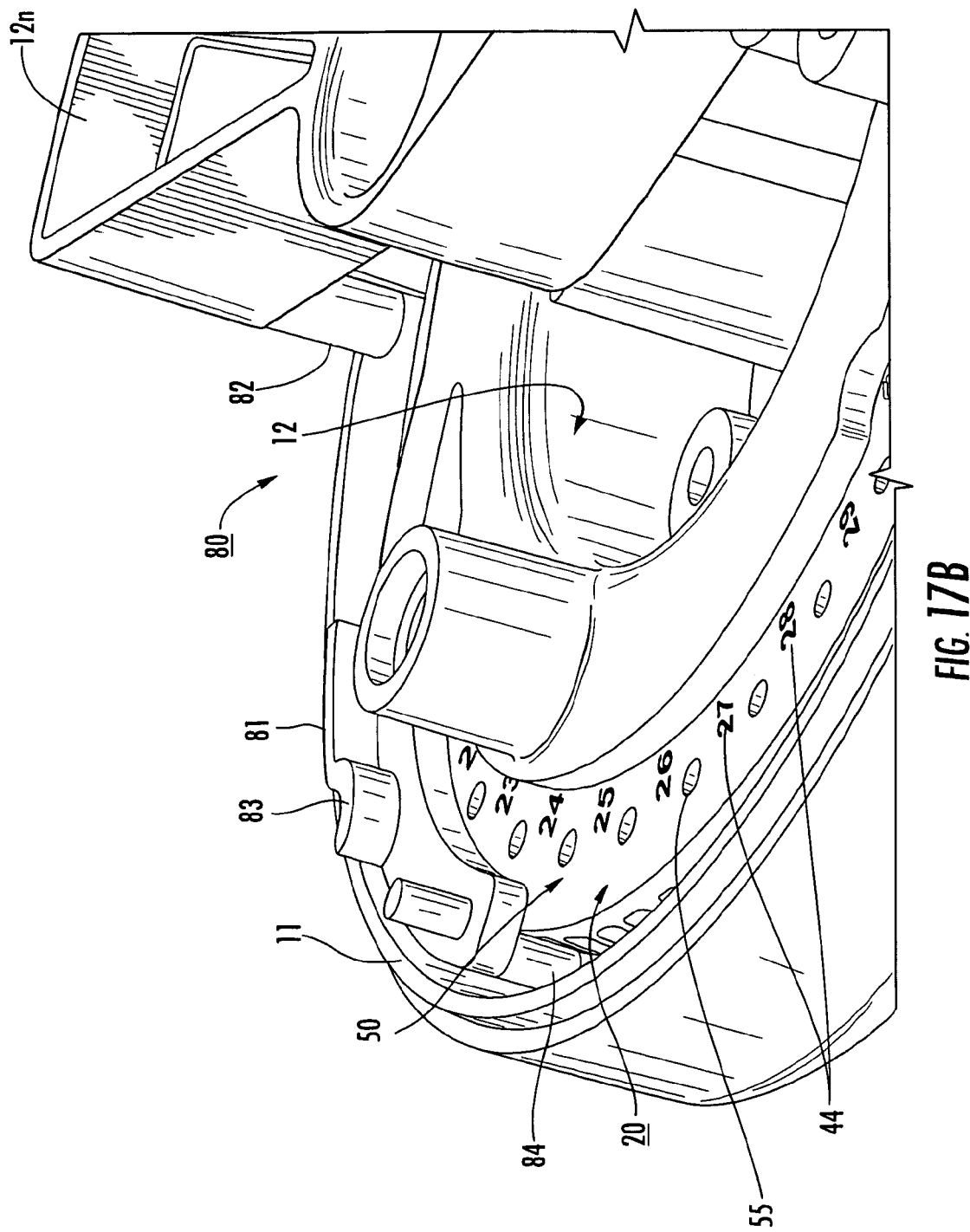
Figure 17C:
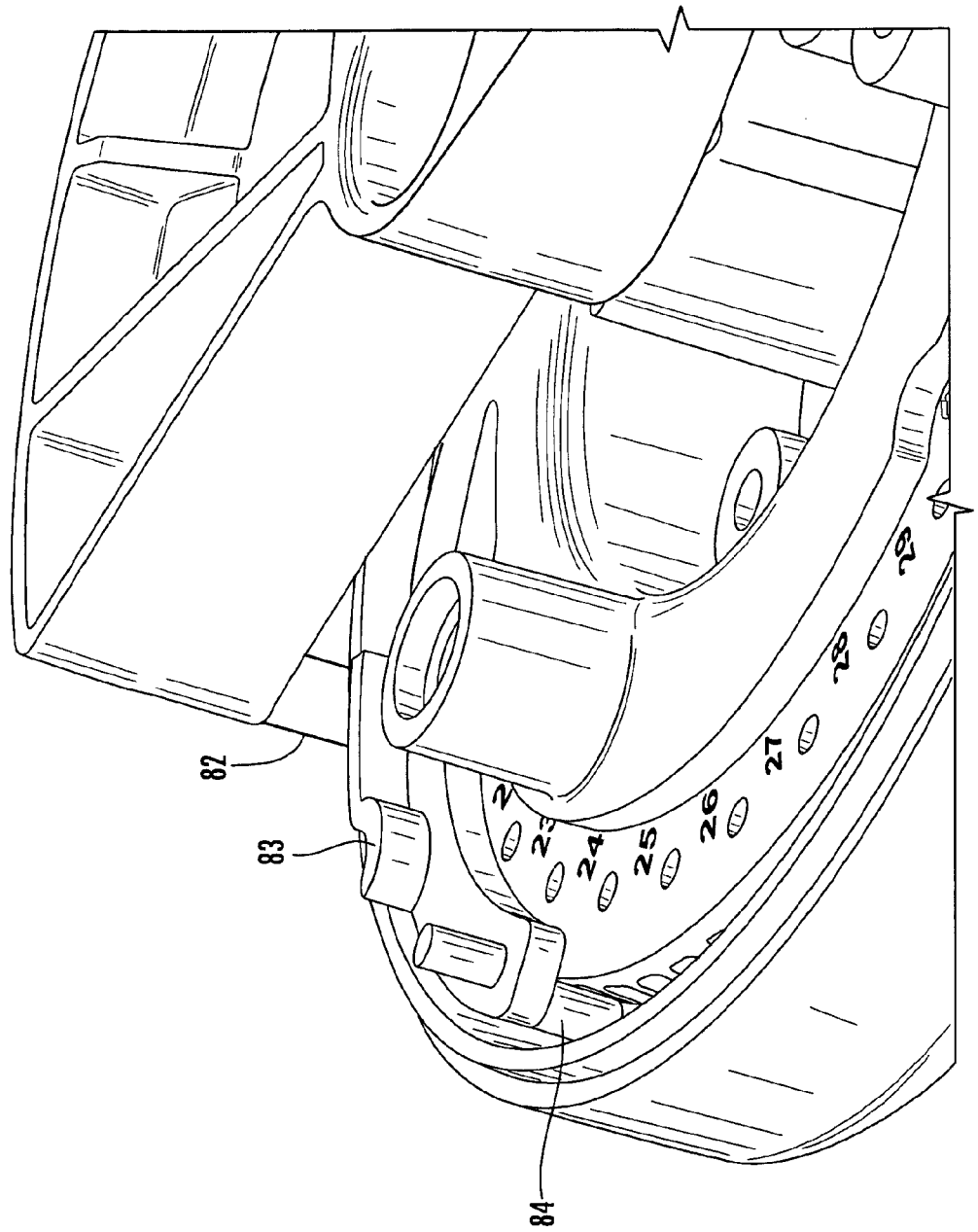
Figure 17E:
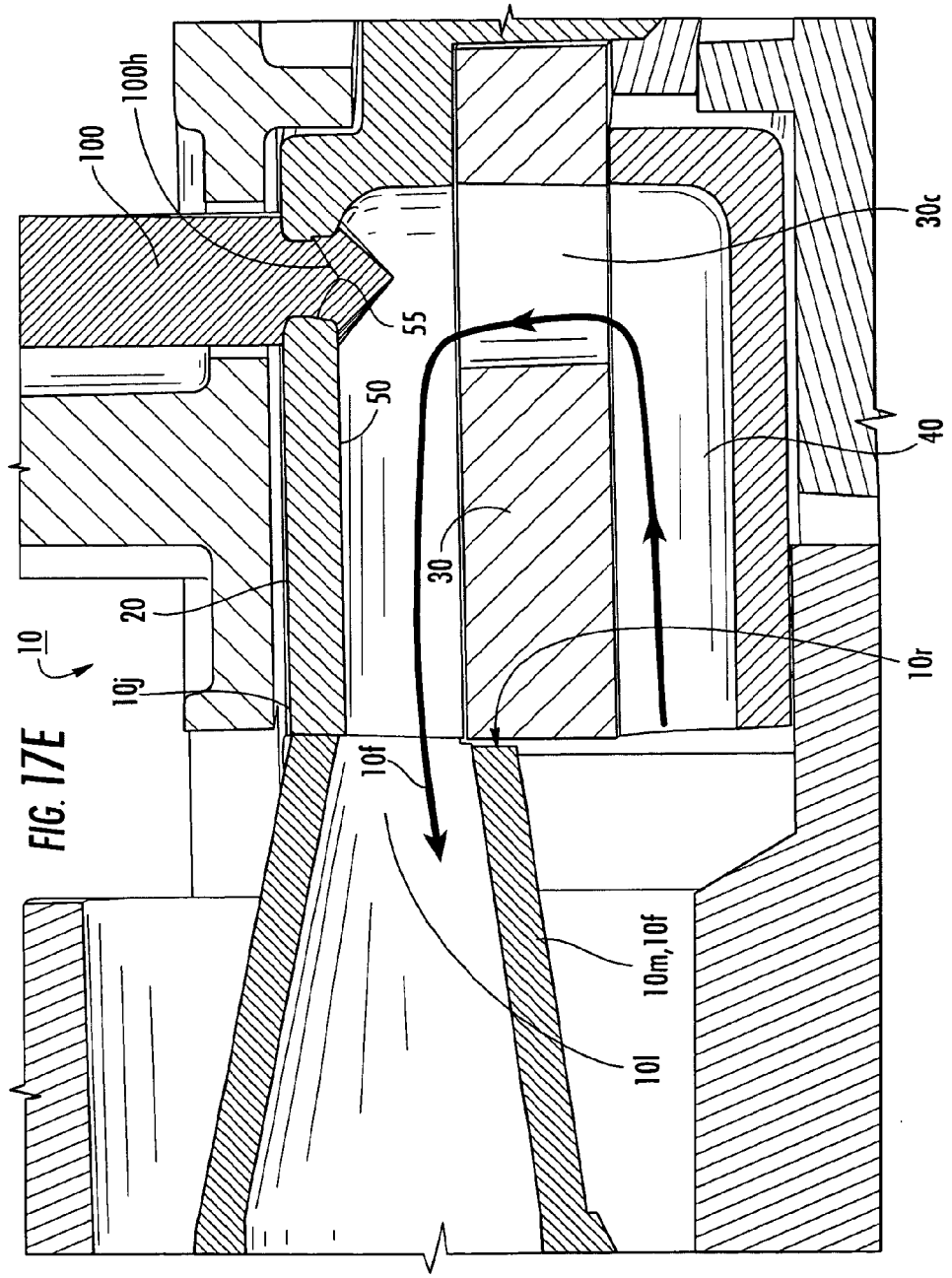
FIG. 17E is a greatly enlarged cutaway view of an airflow path in an inhaler and disk to exit path joint according to embodiments of the present invention.

As shown in FIG. 17B, the lever assembly 80 includes a lever arm 81 that communicates with an upper surface of the upper airway disk 50 and extends down a distance to reside closely spaced to an outer perimeter of the disk assembly 20. The lever assembly 80 also includes a finger 82 that resides above the disk assembly 20 and extends down toward the disk assembly 20. In the embodiment shown, the lever assembly 80 also includes a loading post 84 that resides proximate an outer perimeter of the disk assembly 20. The lever arm 81 includes a recess 83 that is configured to receive the finger 82. As the finger 82 resides in the recess 83, the post 84 post pushes the disk assembly 20 radially inward to causes a tight joint 10j at the time of inhalation (FIG. 17E). The recess 83 can have an open perimeter shape and the finger 82 can slidably enter and exit therefrom. The lever arm 81 can define a ramp (inclined in the direction toward the recess 83) that slidably engages the finger 82 and directs the finger 82 to move toward the recess 83. Other radially biasing means for translating the disk 30 toward the mouthpiece can be used. See, co-pending, co-assigned U.S. application Ser. No. 12/566,799, the contents of which are hereby incorporated by reference as if recited in full herein.

The lever assembly finger 82 is attached to lever 12n (also labeled as 10l in FIG. 17A) and/or 12n and rotates with respect to the frame 12 in the inhaler housing, typically upon user actuation of the lever 12n. When the lever 12n is return from "actuated" (dosing) position, the finger 82 is pulled out of the recess 83 so that the disk assembly 20 is free to rotate to index to a next dispensing position.

Typically during inhalation, the loading post 84 resides radially opposite (substantially diametrically opposed to) the mouthpiece 10m. The lever arm 81 and post 84 do not rotate. This component is affixed to a frame 12 that is attached to the inhaler housing. The finger 82 rotates with respect to the frame 12 (and the lever arm 81).

As shown in FIG. 17B, the finger 82 does not contact the lever arm 81 during this portion of the stroke cycle of the lever assembly 80 to allow for free rotation during indexing. FIG. 17C illustrates the finger 82 moving toward the recess 83. FIG. 17D illustrates the finger 82 in the recess 83 to bias the disk 30 and/or disk assembly 20 toward the exit flow path member 10fm. At the moment of inhalation, the finger 82 is advanced to its fullest extent of travel. Indexing (rotation) of the disk assembly 20 occurs while the arm 83 is elsewhere in its travel path. Therefore, as shown by the arrows in FIG. 17D, the lever assembly 80 can bias the disk assembly 20 while the finger 82 is at the far extent of travel to seal the joint 10j at the proper time (inhalation), while allowing free movement during indexing (typically also unbiased the rest of the time).

It is recognized that, during manufacturing, there may be a tolerance-induced mismatch between the diameters of the dose disk 30 and the upper airway disk 50 of the disk assembly 20. As shown in FIG. 17E, inner or outer sidewall surfaces (shown as outer sidewall surfaces) of both of these disks, 30, 50 contact the mouthpiece 10m when the disk assembly 20 is biased against it. Thus, as shown in FIG. 17E a small relief 10r can be cut or otherwise formed into the proximate or abutting surface of the an exit flowpath member 10fm (which may be the mouthpiece 10m) at a location that coincides with the dose disk 30 to assure that the upper airway disk 50, which has the greater amount of contact surface, is always the part to contact the mouthpiece or exit flowpath member 10fm in communication with the mouthpiece 10m.

FIG. 19A illustrates one embodiment of a piercing mechanism 100 with a corkscrew piercer 110. In operation the corkscrew moves up and down vertically straight, typically without rotation, to create a desired opening shape (e.g., circular) through the sealant layers 36, 37. In other embodiments, the corkscrew may rotate during extension and/or dispensing. In the embodiment shown, the corkscrew piercer 110 can remain in the lower channel 41 while the dry powder is dispensed in the airflow path and the blockage of the aperture 30a can be provided by a resilient member 120 that is mounted on the corkscrew 110 and moves up and down therewith. The piercing mechanism 100 can have a two stage operation, fully up (for indexing) and fully down. The most forward portion of the corkscrew can have a point with a configuration that creates a desired cutting configuration into the sealant (e.g., foil). In some embodiments, the corkscrew piercer 110 can cut a shape with a tab into the sealant 36, 37, then fold the tab down to release the dry powder. Positioning the corkscrew piercer 110 in the channel 41 during dispensing may provide improved aerodynamics or shear or impaction flow turbulence for the dry powder. The resilient member 120 can comprise a foam block or other resilient member 120 that can be used to seal or plug the aperture 30a. FIG. 19B illustrates a similar corkscrew piercer 110 that is used with a disk assembly 20 having both upper and lower airway disks 50, 40. A resilient and/or flexible member 100p such as a polymeric and/or elastomeric or foam plug can be used to occlude or seal the disk aperture 55.

FIGS. 19C and 19D illustrate a piercing mechanism 100 with a fluted solid piercer 111. The flute may have a straight flute configuration or the flute can have a twist or partial twist along it length, e.g., the maxima and minima of the lobes change axially along the length of the flute. The flute can have a cross section with a plurality of lobes, typically three or four lobes, shown as three lobes in FIG. 19C and four lobes 111' in FIG. 19F and the aperture 55 can have a corresponding shape (e.g., a perimeter shape with three our four lobes). The fluted configuration may extend only a partial forward length and merge into a constant diameter segment that resides in and helps occlude or seal the aperture 55 as shown in FIG. 19E. In other embodiments, the solid or fluted piercer configuration can merge into a cap or plug 100p that resides over and/or in the aperture 55 (see, e.g., FIG. 19C). In some embodiments, the twisted flute 111 can remain in the lower disk 40 during dispensing which may facilitate turbulence and/or compaction in the airway.

FIG. 19D illustrates that the fluted piercer 111 can rotate as it pierces the foil or other sealant material to form a round hole or may be extended straight without rotation. In other embodiments, the fluted piercer 111 can be extended or advanced without rotation to pierce the sealant layer(s) 36, 37. FIG. 19E illustrates that the fluted piercer 111' can include a fluted forward portion 111f with a length "$L_1$" that merges into a solid portion 112 that can have a substantially circular cross-section with a length "$L_2$". $L_1$ is typically longer than $L_2$. $L_1$ can have a length sufficient to allow the forward fluted portion 111f to reside in the dose container aperture 30a (typically just below the upper sealant line or in-line with or slightly above or below the lower surface of the disk 30) and/or through the lower sealant 37 at the same time, with the solid portion engaging the airway disk aperture 55.

As noted above, in some embodiments, the fluted piercer 111 can be configured with lobes that twist along its length (FIG. 19D). For example, the fluted piercer 111 can have about 60 degrees of twist along its length such that the lobes of the fluted piercer turn about its circumference. During a straight piercing stroke (straight into and through the sealant), the twisted fluted piercer 111 can make a fully round hole in the sealant 36 and/or 37.

Figure 19G:
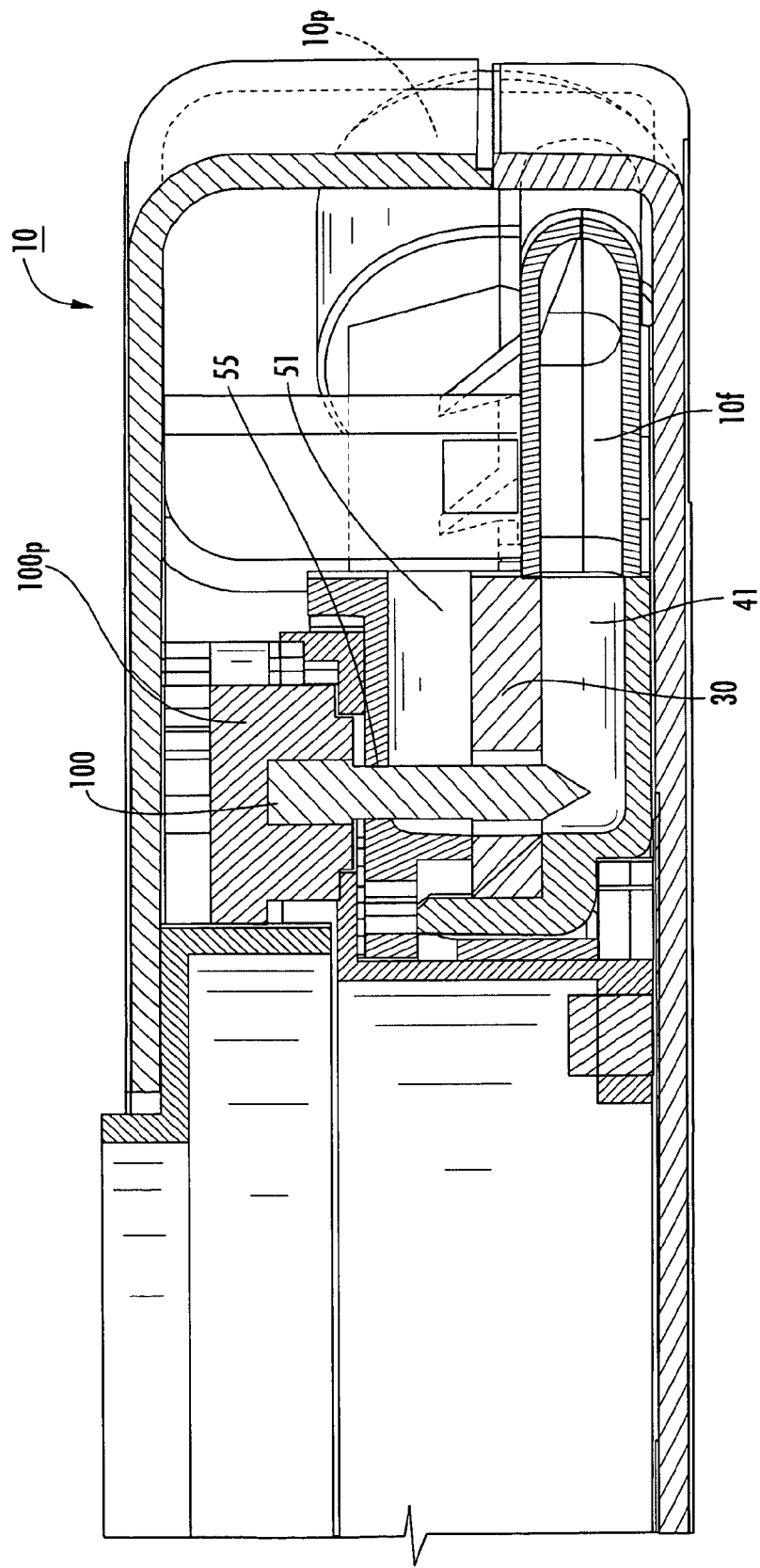
FIG. 19G is a partial cutaway schematic illustration of an inhaler with a piercer according to some embodiments of the present invention.

FIG. 19G illustrates a piercing mechanism 100 that can include a plug 100p (similar to that shown in FIG. 19B for the corkscrew configuration) that can occlude the passage 55. The plug 100p can be used with any piercer, including the corkscrew 110 (FIG. 19A) or the solid fluted piercer 111 (FIG. 19B) or other piercer configuration. The piercing head can remain in the lower channel 41 during dispensing as shown in FIG. 19E, or the piercer may retract partially through a passage in the plug (not shown) while leaving the plug 100p in position against and/or over the aperture or passage 55.

The inhaler 10 can include a user-accessible actuator such as a lever, knob, switch, slider, crank, pushbutton or other mechanical and/or electromechanical device that can index the dose ring or disk 30 to rotate the assembly 20 to place one or more dose containers 30c (FIG. 2B) in a dispensing position in an inhalation chamber in fluid communication with the inhalation port 10p (FIG. 1) and/or cause a piercing mechanism 100 (FIGS. 7A-7C) to open a dose container 30c in the front row, then the back row (or vice versa) to release medicament to an inhalation air flow path for inhalation by a user (as will be discussed further below). To release the powder for inhalation, the sealed dose container 30c is opened and connected to an airway 41 and/or 51 which is in turn connected to the inhaler mouthpiece 10m (see, e.g., FIGS. 7A-7C, 17A, 18A). After the drug falls into the channel 41 or 51 (depending on which orientation the inhaler is in), this is a "used" channel and the drug therein is either delivered (if the user inhales properly and timely) or isolated (if the user does not inhale and closes the mouthpiece or otherwise causes the indexing of the disk assembly 20), and the "used" channel is indexed with the opened dose container 30c so that it cannot be used again or so that it is used again for only the other dose container in the shared channel (as discussed with respect to FIG. 2C). Any powder remaining in the opened dose container is separated from the airway when the next dose container is indexed into position.

In some embodiments, the portion of the airway provided by the airway channel 41 or 51 adjacent to each dose container 30c is unique to that individual dose container 30c. In this way, any spillage of powder into the airway will only be available to the mouthpiece and user as long as that dose container is indexed into connection with the primary (mouthpiece) airway. Indexing to the next dose container will also index the adjacent airway section out of connection with the active inhalation airway path, taking any spilled and/or accumulated powder with it.

Figure 8A:
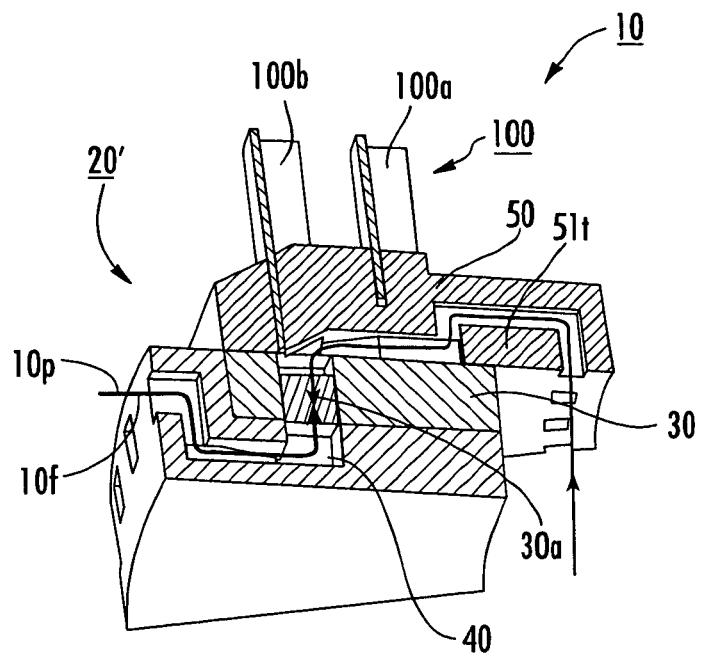
FIG. 8A is a bottom perspective partial cutaway view of an inhaler with a dose container assembly configured so that the outer ring of dose containers are aligned with airway channels in disks that have "sink traps" to inhibit spillage according to some embodiments of the present invention.
Figure 8B:
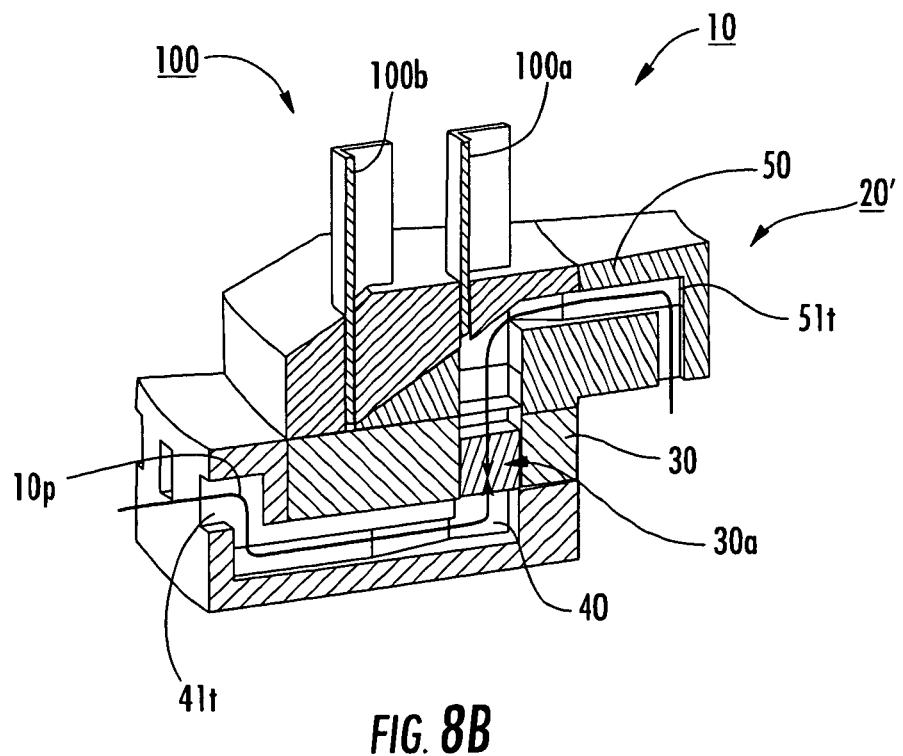
FIG. 8B is a side perspective view of the device shown in FIG. 8A illustrating the inner row of dose containers are aligned with airway channels in disks that define "sink traps" to inhibit spillage according to some embodiments of the present invention.
Figure 9A:
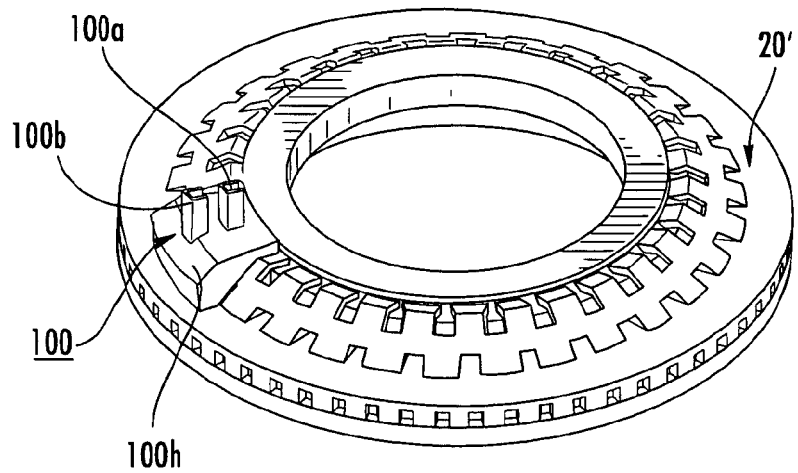
FIG. 9A is a top perspective view of a dose container assembly and piercing mechanism according to some embodiments of the present invention.
Figure 9B:
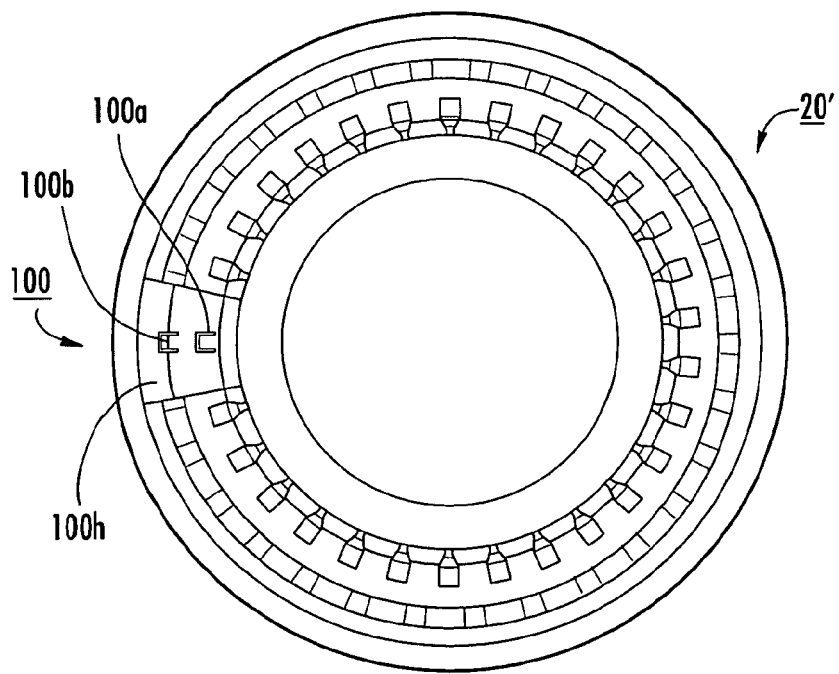
FIG. 9B is a top view of the device shown in FIG. 9A.
Figure 9C:
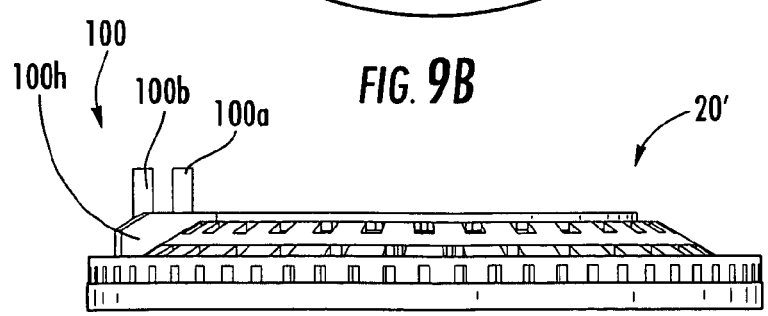
FIG. 9C is a side view of the device shown in FIG. 9A.
Figure 13:
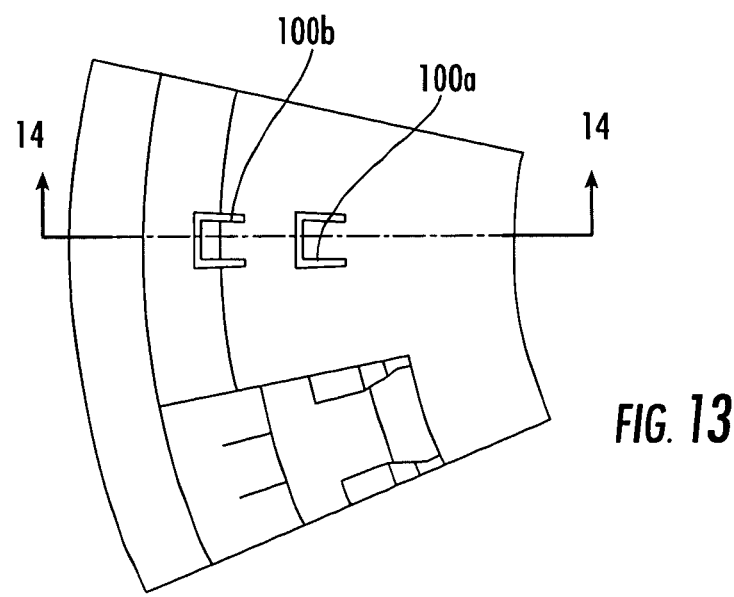
FIG. 13 is a top assembled view of the portion of the device shown in FIG. 10.

FIGS. 8A and 8B illustrate another embodiment of an inhaler 10. In this embodiment, the upper airway channel 51 can be configured as a "sink trap" 51t path that has a portion of the airflow path that rises and then turns down or vice versa. That is, as shown, the path 51t can rise above the aperture 30a, then turn to extend downwardly for a distance to provide additional spill resistance of the dry powder from the airway/inhaler. Similarly, the lower airway channel 41 can be configured to rise upward a distance downstream of the dose container aperture 30a to form a "sink trap" 41t path. In some embodiments, only one of the airway disks (e.g, the upper or the lower 50, 40) have a sink trap path while in others, both disks 40, 50 have airway configurations with sink traps 41t, 51t as shown. The dose container assembly 20 has an aligned channel pair 41, 51 that are in fluid communication once the respective dose container is opened 30c that reside under and over the respective dose container 30c and have the sink trap configurations 41t, 51t to that cooperate to form a curvilinear airflow path (e.g., a generally "S" shape, with the "S" layed on its side).

As also shown in FIGS. 8A and 8B, in this embodiment, the piercing mechanism 100 can include two piercing members 100a, 100b, one dedicated to opening the first row of dose containers 30c and another for the second row of dose containers 30c.

FIGS. 9A-9C and 10-14 illustrate an exemplary inhaler configuration with upper and lower airways forming a sink trap 51t, 41t airflow path according to embodiments of the present invention. As shown, the piercing mechanism 100 can include the two piercing members 100a, 100b mounted on a housing that slides over the dose container assembly 20'. The dose container assembly 20' can rotate under the piercing mechanism 100 as a respective dose container(s) 30c is indexed to a dispensing position. Similarly, the dose container assembly 20' can rotate above the piercing mechanism if the piercing mechanism is below the dose container assembly 20, 20'.

Figure 14:
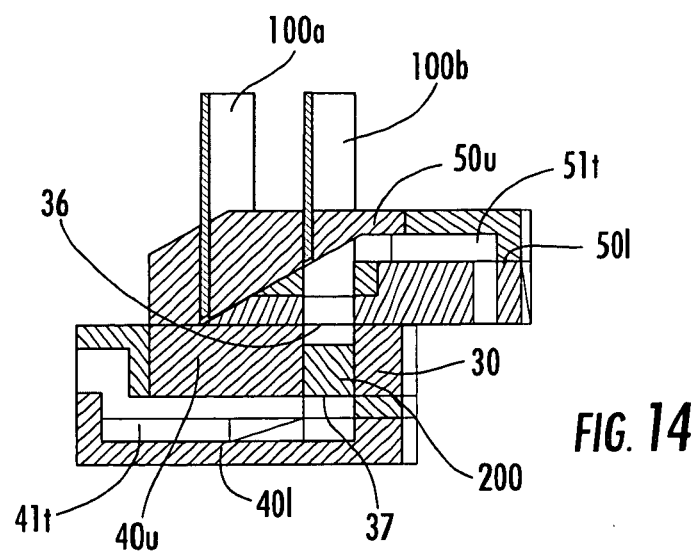
FIG. 14 is a side section view taken along lines 14-14 of FIG. 13, illustrating an inner ring actuation according to embodiments of the present invention.

FIGS. 10, 12 and 14 illustrate that the lower airway disk 40 can include two components, an upper member 40u and a lower member 40l that attach to define the curvilinear sink trap paths 41t. Similarly, the upper airway disk 50 can include two components, an upper member 50u and a lower member 50l that attach to define the curvilinear sink trap paths 51t. In particular embodiments, the dry powder can be provided as a pre-measured amount of dry powder 200 and sealed in the aperture 30a between the sealant layers 36, 37. As shown in FIG. 10, the upper member 50u can include a tab 150t that engages a slot 150s in the lower member 50l of the airway disk 50 for alignment and/or attachment.

FIG. 12 illustrates a dose container 30c on the outer row 31 being opened with the piercing member 100b and the associated curvilinear airflow path 41t, 51t. FIG. 14 illustrates the piercing member 100a in position to open a dose container 30c on the inner row 32 with the associated airflow path 41t, 51t.

Figure 15A:
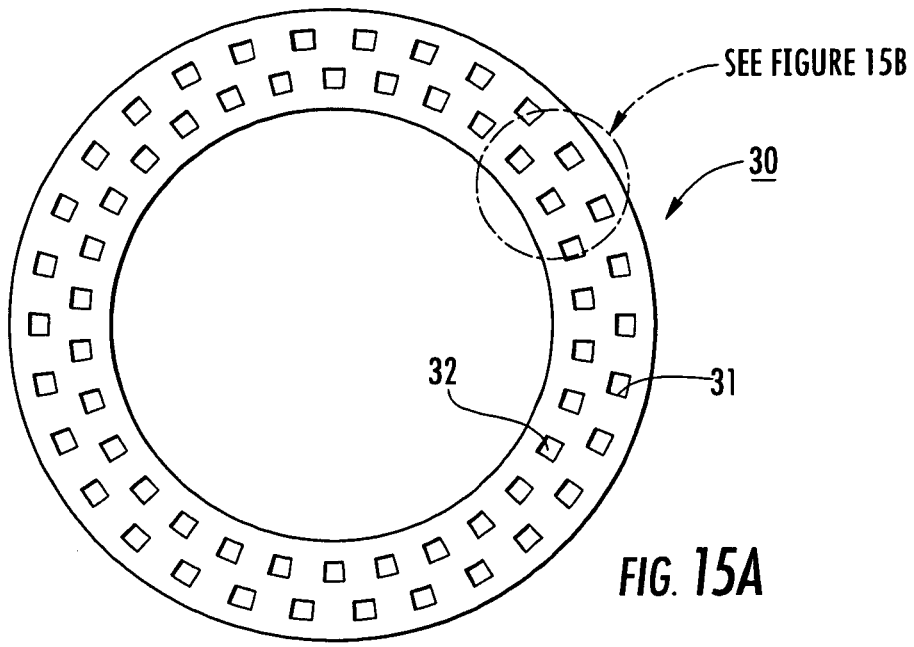
FIG. 15A is a top view of a dose container ring according to some embodiments of the present invention.
Figure 15B:
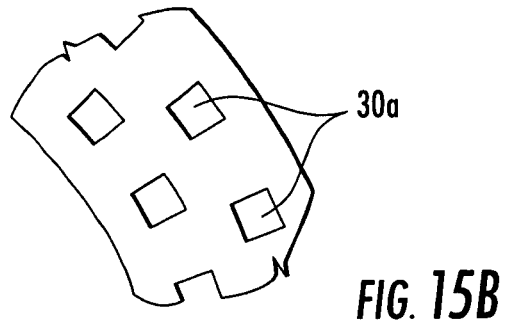
FIG. 15B is a partial enlarged fragmentary view of the ring shown in FIG. 15A.
Figure 16:
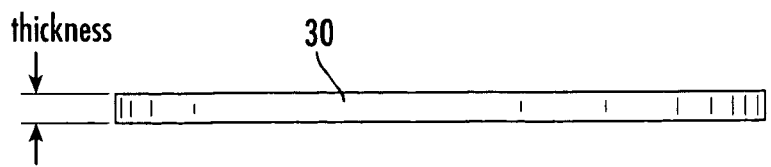
FIG. 16 is a side view of the ring shown in FIG. 15A.

FIGS. 15A, 15B and 16 illustrate an example of a dose container disk or ring 30 with two rows of apertures 30a used for dose containers 30c. The dose container disk 30 can be relatively thin, such as about 2-4 mm thick. The dose container apertures 30a can be configured so that the inner row 32 is at least about 2 mm from the outer row 31 and so that the inner and outer rows of dose containers are spaced inward from the respective perimeters by about 2 mm. This spacing can provide sufficient moisture permeability resistance and/or oxygen resistance.

FIG. 17A illustrates on embodiment of an inhaler 10 with a long exit air path 10l compared to the shorter flow path in FIG. 18A. In this embodiment, the airway disks can orient the channels 41, 51 so that the open ends 41b, 51b face and open to the inside of the disk rather than the outside. FIG. 17A also illustrates that the dose container disk 30 can be configured with blisters 130.

FIG. 17A also illustrates that the piercing mechanism 100 can comprise a rotating piercer head 102 configured to pierce a dose container 30c on the inner row, then rotate to pierce the adjacent one 30c on the outer row.

Figure 18B:
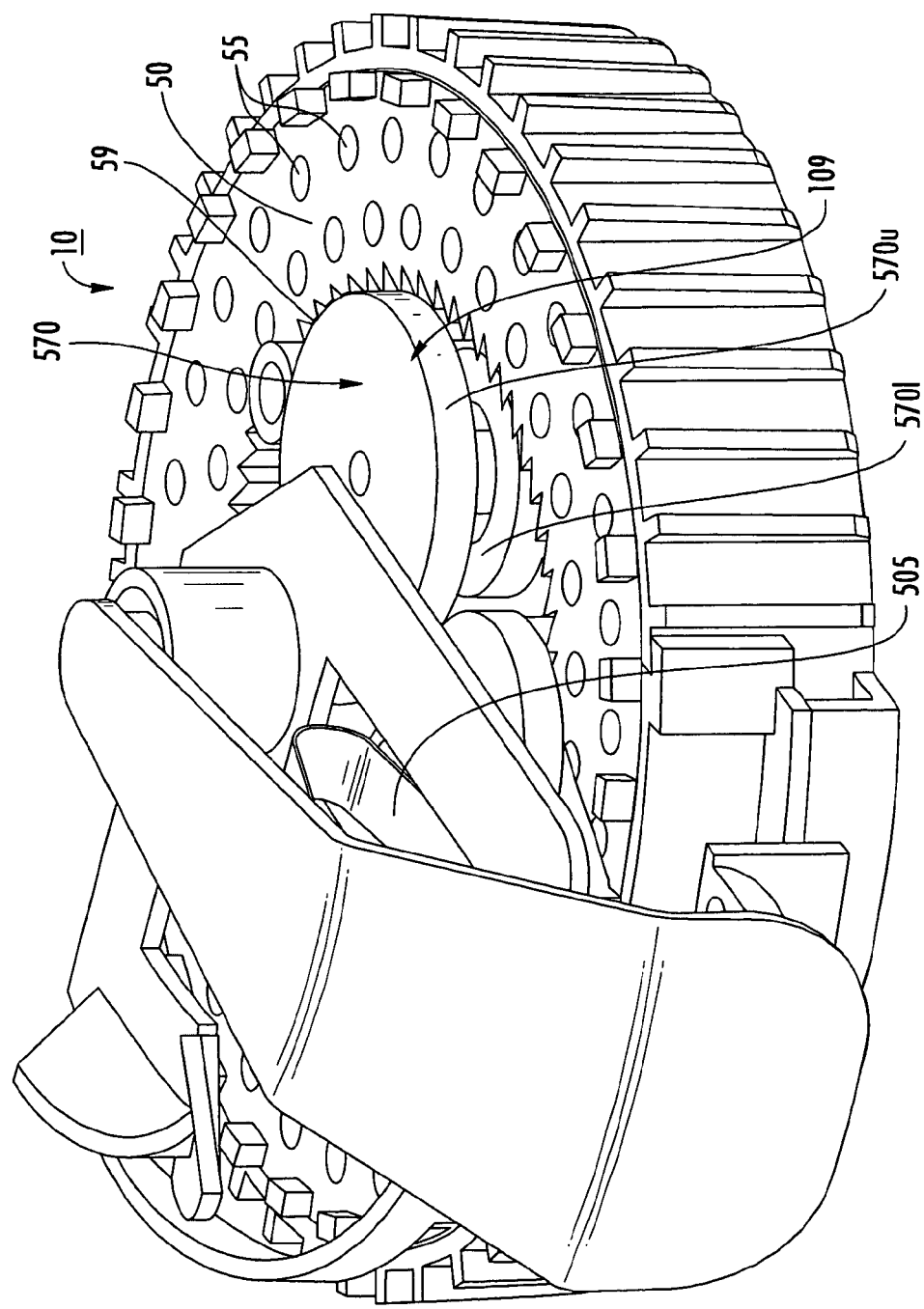
FIG. 18B is a greatly enlarged partial cutaway view of the inhaler shown in FIG. 18A illustrating an indexing mechanism according to some embodiments of the present invention.

As will be discussed further below, FIG. 18A illustrates that the inhaler can be configured with a piercing mechanism 100 that moves radially (e.g., is radially biased), typically with a spring 500 (but other elastic or resilient members may be used) to open a dose container 30c in one row then move radially inward or radially outward to open a dose container 30c in the other row. FIGS. 18A, 18B also illustrate that the inhaler 10 can include an indexing mechanism 109 that cooperates with the gear teeth 59 on the inner perimeter of the upper disk 50. Other indexing mechanisms may be used to rotate the assembly 20 or dose disk 30, where used alone, to place the different dose containers 30c in the dispensing position.

Thus, in some embodiments, the mouthpiece port 10p and an air inlet port (not shown) may be spaced apart about a distance of between about 12-127 mm (about 0.5-5 inches). The inhaler 10 may have a relatively short air intake airpath (measured from where an air intake is disposed to the inhalation port 10p), such as between about 12-25.4 mm such as shown in FIGS. 7A-7C and 18A, or a longer airpath such as shown in FIG. 17A, typically between about 50-127 mm (about 2-5 inches). The shorter airpath can be defined to include a short tubular airpath extending between the dry powder release location and the inhalation mouthpiece with a turbulence promoter segment that inhibits agglomeration that merges into the inhaler mouthpiece (not shown). The longer airpath may extend across a major portion or substantially all of a width or length of the inhaler body. For a more detailed discussion of suitable turbulence promoter configurations, see PCT/US2005/032492, entitled, Dry Powder Inhalers That Inhibit Agglomeration, Related Devices and Methods, the contents of which are hereby incorporated by reference as if recited in full herein.

The inhaler 10 can have a body that is a portable, relatively compact "pocket-sized" configuration. In some embodiments, the inhaler body can have a width/length that is less than about 115 mm (about 4.5 inches), typically less than about 89 mm (about 3.5 inches), and a thickness/depth of less than about 51 mm (about 2 inches), typically less than about 38 mm (about 1.5 inches). The inhaler body can also be configured to be generally planar on opposing primary surfaces to facilitate pocket storage.

The inhaler can include a circuit that can control certain operations of the inhaler 10. The inhaler 10 can include a computer port (not shown). The port may be, for example, an RS 232 port, an infrared data association (IrDA) or universal serial bus (USB), which may be used to download or upload selected data from/to the inhaler to a computer application or remote computer, such as a clinician or other site. The inhaler 10 can be configured to via a wired or wireless communication link (one-way or two-way) to be able to communicate with a clinician or pharmacy for reorders of medicines and/or patient compliance. The inhaler 10 may also include a second peripheral device communication port (not shown). The inhaler 10 may be able to communicate via the Internet, telephone, cell phone or other electronic communication protocol.

In some embodiments, the circuit can include computer program code and/or computer applications that communicate additional data to a user (optionally to the display) as noted above and/or communicate with another remote device (the term "remote" including communicating with devices that are local but typically not connected during normal inhalant use).

In some embodiments, the circuit can be in communication with a vibrator device (not shown). The vibrator device can be any suitable vibrator mechanism. The vibrator device can be configured to vibrate the dry powder in the airflow path. In some embodiments, the vibrator device can comprise a transducer that is configured to vibrate the opened cartridge(s) holding the dry powder. Examples of vibrator devices include, but are not limited to, one or more of: (a) ultrasound or other acoustic or sound-based sources (above, below or at audible wavelengths) that can be used to instantaneously apply non-linear pressure signals onto the dry powder; (b) electrical or mechanical vibration of the walls (sidewalls, ceiling and/or floor) of the inhalation flow channel, which can include magnetically induced vibrations and/or deflections (which can use electromagnets or permanent field magnets); (c) solenoids, piezoelectrically active portions and the like; and (d) oscillating or pulsed gas (airstreams), which can introduce changes in one or more of volume flow, linear velocity, and/or pressure. Examples of mechanical and/or electro-mechanical vibratory devices are described in U.S. Pat. Nos. 5,727,607, 5,909,829 and 5,947,169, the contents of which are incorporated by reference as if recited in full herein. Combinations of different vibrating mechanisms can also be used.

In some embodiments, the vibrator device can include a commercially available miniature transducer from Star Micronics (Shizuoka, Japan), having part number QMB-105PX. The transducer can have resonant frequencies in the range of between about 400-600 Hz.

In certain embodiments, the inhaler 10 can include visible indicia (flashing light or display "error" or alert) and/or can be configured to provide audible alerts to warn a user that a dose was properly (and/or improperly) inhaled or released from the inhaler. For example, certain dry powder dose sizes are formulated so that it can be difficult for a user to know whether they have inhaled the medicament (typically the dose is aerosolized and enters the body with little or no taste and/or tactile feel for confirmation). Thus, a sensor (not shown) can be positioned in communication with the flow path in an inhaler and configured to be in communication with a digital signal processor or microcontroller, each held in or on the inhaler. In operation, the sensor can be configured to detect a selected parameter, such as a difference in weight, a density in the exiting aerosol formulation, and the like, to confirm that the dose was released.

The sealed dose containers 30c can be configured so that the water vapor transmission rate can be less than about 1.0 g/100 in²/24 hours, typically less than about 0.6 g/100 in²/24 hours and an oxygen transmission rate that is suitable for the dry powder held therein. The dose container assemblies 20, 20' can be configured with a stable shelf life of between about 1-5 years, typically about 4 years.

The dose containers 30c can have a volume (prior to filling and sealing) that is less than about 24 mm³, typically between 5-15 mm³. The powder bulk density can be about 1 g/cm³ while the power nominal density when filled (for reference) can be about 0.5 g/cm³. The maximum compression of a drug by filling and sealing in the dose container 30c can be less than about 5%, typically less than about 2%. The maximum heating of drug during the filling and sealing can be maintained to a desirable level so as not to affect the efficacy of the drug or the formulation.

FIG. 20 illustrates exemplary operations that can be used to operate an inhaler according to embodiments of the present invention. The device can be configured to have an automated three-stage operation at actuation to inhibit overdose delivery, e.g., it can serially: (a) pierce the sealant layers, (b) release the drug (typically followed by delivery), and (c) index to the next (unopened) dose container (thus isolating or closing any exit route for the released dry powder if not inhaled); or (a) index to a target dose container (thus isolating an earlier opened airway channel), (b) pierce the sealant layers and (c) release drug or dry powder from the opened dose container. A dose container ring having a staggered concentric arrangement of dose container apertures sealed by upper and lower sealant layers defining dose containers and attached to an underlying disk with a plurality of circumferentially spaced apart airway channels, one for each dose container, is provided (block 300). The dose container with the underlying disk is rotated to a dispensing position in the inhaler (block 310). The airway channel associated with the released dry powder is isolated from the inhalation path so that the used airflow channel is not used for any subsequent inhalation delivery or is used only one more time (block 325).

In some embodiments, a piercing mechanism is advanced to open both sealant layers and release dry powder from the dose container in the dispensing position to the underlying airway channel (block 320). The piercing mechanism can either remain extended or can be partially or fully retracted with the piercing mechanism or cooperating member thereof occluding the opening to the upper airway channel. In some embodiments, the piercing mechanism can be partially retracted, leaving at least a forward portion in the respective dose container aperture to occlude and/or plug the aperture. The isolating step can be in response to and/or after either the step of fully retracting the piercing mechanism from the dose container aperture (block 350) or the rotating step (block 310) or both.

The method can also optionally include flowably directing the released dry powder to a user via the airway channel.

Figure 21:
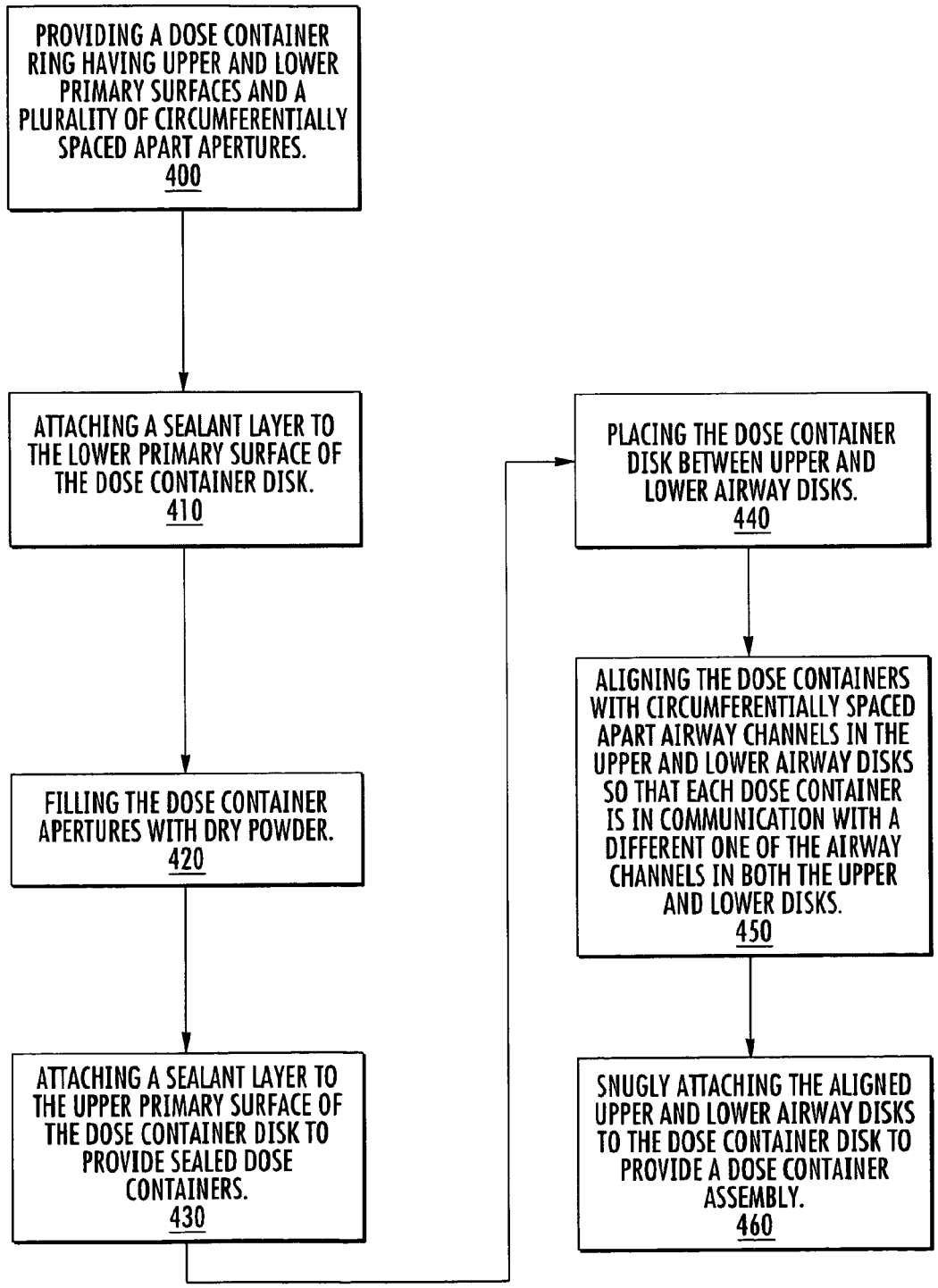
FIG. 21 is a flow chart of operations that can be used to fabricate or assemble a dose container assembly according to some embodiments of the present invention.

FIG. 21 illustrates exemplary fabrication operations that can be used to assemble a dose container assembly according to embodiments of the present invention. As shown, a dose container disk (block 400) with circumferentially spaced apart apertures is provided. At least one sealant layer is attached to the upper or lower primary surface of the disk over or under the dose container apertures (block 410) (e.g., a continuous layer or strips or small pieces of sealant layers can be positioned over the apertures). The dose container apertures are filled with dry powder (noting "filled" does not require volumetrically full) (block 420). Typically, the powder is filled to between about 30-75% volume. Attaching a sealant layer to the other primary surface of the dose disk to provide sealed dose containers (block 430). Placing the dose container disk between upper and lower airway disks (block 440). Aligning dose containers with circumferentially spaced apart airway channels on the airway disks so that each dose container is in communication with a different one of the airway channels in both the upper and lower disks (block 450). Snugly attaching the upper and lower disks to the dose container disk to provide a dose container assembly (block 460).

FIGS. 22A-29 illustrate an example of a piercing mechanism 100' that can be used to open dose containers 30c on a dose ring 30. This embodiment may be particularly suitable for dose container rings or disks 30 having multiple rows of dose containers 30c, such as those in a staggered concentric arrangement, e.g., circumferentially spaced apart dose containers 30c on inner and outer rows, 31, 32, with centerlines of the dose containers on the inner and outer rows offset from each other, to access each dose container 30c for opening and inhalation of a dose associated therewith. FIGS. 22A-29 illustrate an inhaler with a mechanism 100' that can index the dose ring or disk 30 the same amount each time, and alternate between piercing a dose container 30c on an inner row with piercing a dose container on the outer row (or vice versa).

The piercing mechanism 100' can be mounted in the inhaler 10 and be radially biased to be able to reciprocally travel radially inward and outward to serially open a dose container 30c on the inner row 32, then one on the outer row 31 or vice versa. Typically, the piercing mechanism 100' is radially biased to want to extend radially outward in the direction of the outer perimeter or outer diameter of the dose container disk 30 or disk assembly 30.

Figure 25A:
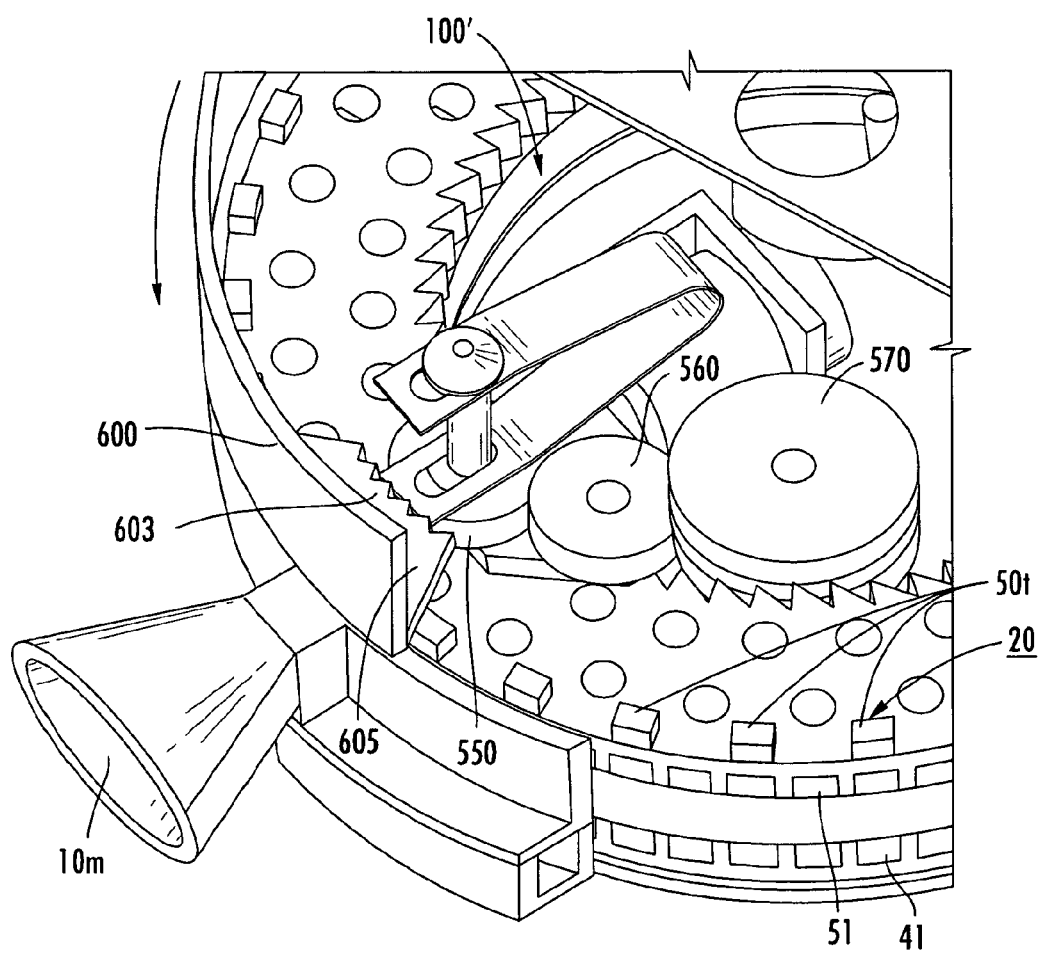
FIG. 25A is a partial cutaway top perspective view of the piercing mechanism shown in FIGS. 22A and 22B illustrating an actuation lever that communicates with a cam surface to push the piercer carriage according to some embodiments of the present invention.
Figure 25B:
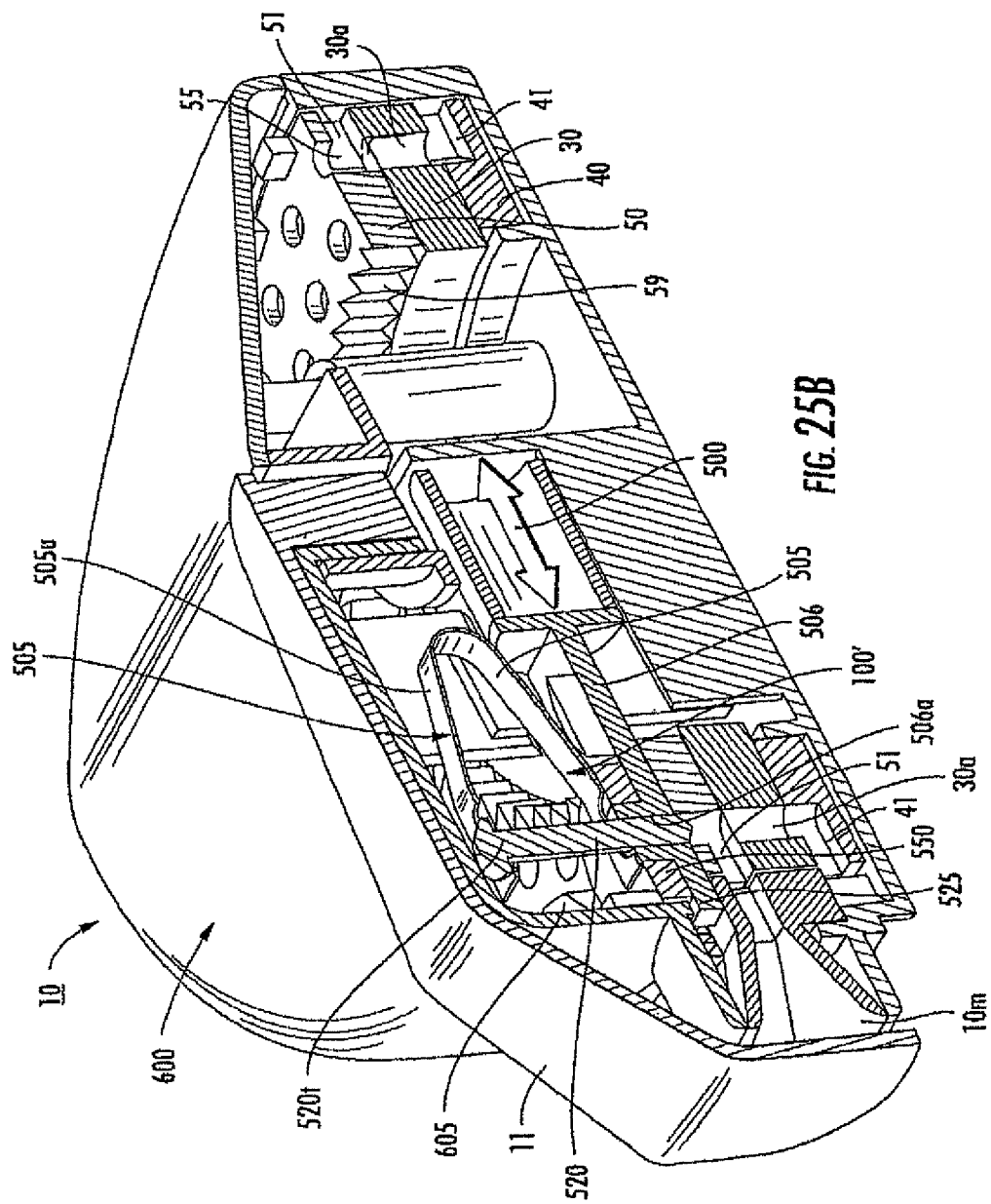
FIG. 25B is a side section view of the piercing mechanism in an inhaler according to some embodiments of the present invention.

Referring to FIGS. 22A-22B and 25B, the piercing mechanism 100' includes a piercer carriage 505 that holds a piercer 520. As shown, the piercer carriage 505 is in communication with an elastic resilient member 500, typically comprising a coil spring 500s that can push substantially horizontally (when held in a normal operative position) against the carriage 505 to bias the piercer carriage 505 in a defined direction (shown as radially outward). The resilient and/or flexible member 500 can be elongate and oriented to extend horizontally with a sufficient spring constant or similar parameter depending how configured to radially bias the piercer carriage 505 outward from a center of the inhaler 10 and/or disk 30. In other embodiments, the piercer carriage 505 can be mounted to the outside of the disk 30 and/or disk assembly 20 (where used) and radially biased in an inward direction (not shown).

Figure 24:
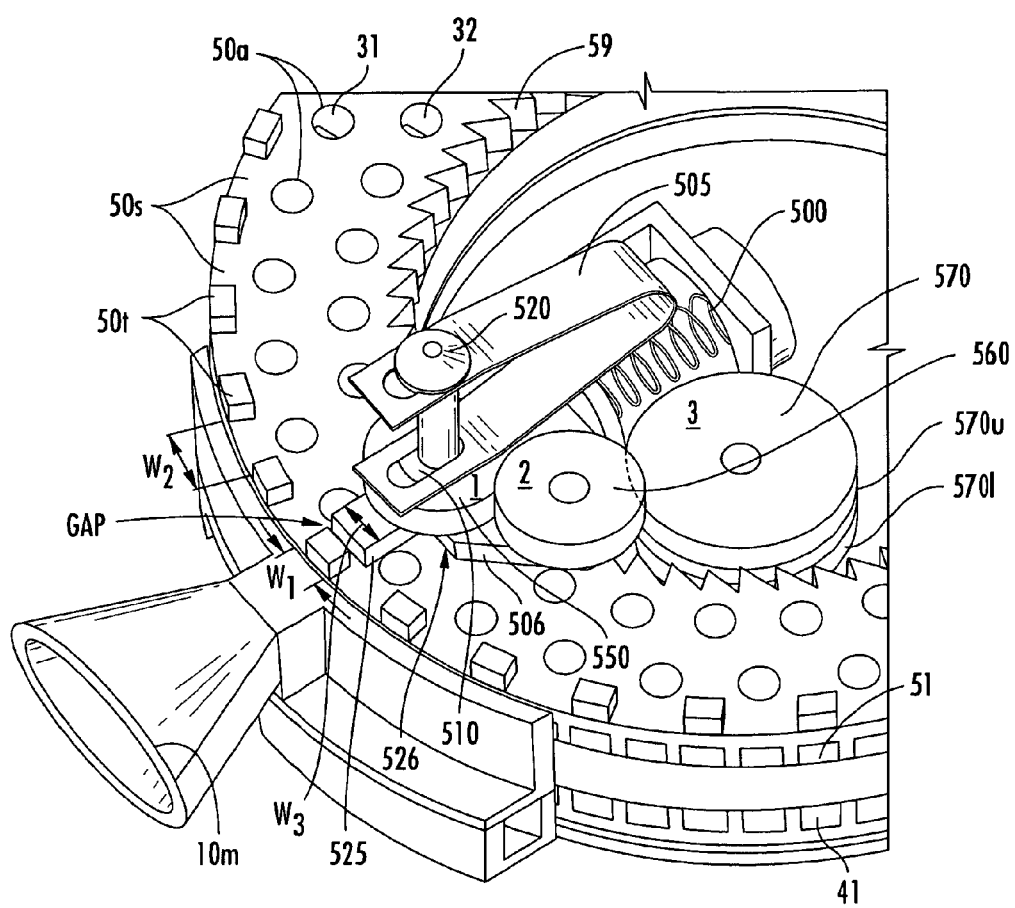
FIG. 24 is a partial cutaway top perspective view of the piercing mechanism shown in FIGS. 22A and 22B illustrating the piercer carriage biased inwardly to engage an idler gear according to embodiments of the present invention.

Referring to FIGS. 24 and 25B, the piercer carriage 505 can include a platform 506 that resides above the upper airway disk (where used) and/or above the dose container disk 30 and a holding member 505u. The member 505u and/or piercer 520 may be mounted to the platform 506 (or otherwise mounted in the inhaler) to hold the piercer 520 while allowing the piercer 520 to travel vertically to open the underlying or overlying dose container 30c. The piercer 520 and/or holding member 505u may also be held and/or constrained in walls or cavities of the inhaler housing to orient and/or help guide the piercer 520 to desired operative positions. The piercer holding member 505u can comprise a spring that can elastically compress in operation while allowing the piercer to travel downward or upward to open the dose container. As shown, the piercer holding member 505u is a "U" shaped leaf spring, but a coil spring or other elastic configuration may also be used. The platform 506 of the piercer carriage 505 is in communication with the resilient member 500 and can "float" in a radial direction to be able to reciprocally slidably travel inward and outward a distance appropriate to align over a dose container 30c on the inner row 32, then one on the outer row 31 (or vice versa).

Still referring to FIGS. 24 and 25B, the platform 506 can hold the member 505u and include an aligned aperture 506a that allows the piercer 520 to vertically slidably extend and retract therethrough. The platform 506 can include a forward portion 525 having a width "W3" that radially and/or circumferentially aligns the piercer 520 with the target dose container row 31, 32, respectively. In some embodiments, the platform 506 can also hold a drive gear 550 that cooperates with an actuation member 600 (FIGS. 26, 28, 29) with a cam surface 606 and gear teeth 608 to rotationally index the dose disk 30 in the inhaler 10 as will be discussed further below. The platform 506 forward member 525 engages upwardly extending tabs 50t or extends between tabs 50t into spaces 50s, typically held on a disk, shown as on the upper airway disk 50, but the tabs may be positioned on the dose container disk 30 or a disk overlying and attached thereto where such is used without requiring an upper airway disk. Alternately, the tabs 50t may be on the outer perimeter of the lower airway disk if the piercer mechanism 100' is configured to pierce bottom-up, rather than top-down (shown in the figures as top-down in normal operation).

Referring to FIG. 24, the forward member 525 has a width W3, the tabs 50t have a width W1, and the spaces 50s have a width W2. Typically, W3 is greater than or equal to W1 (but can be less than W1 as well). W3 is typically less than W2. In operation, as the disk 30 (and/or disk assembly 20) is rotationally indexed to an inhalation position, the forward member 525 can slide forward to contact a tab 50t or enter a space 50*s* between adjacent tabs 50*t*. The shoulder 526 of the forward member 525 engages the adjacent tabs 50*t* when the forward member 525 enters the space 50*s* as shown in FIG. 22A. When the forward member 525 contacts a tab 50*t*, the piercer 520 is radially and circumferentially positioned over the inner dose container row 32; when the forward member 525 enters a space 50*s*, the piercer 520 is positioned over the outer dose container row 31.

FIGS. 23A illustrates one embodiment where the forward member 525 has a cross-section that is substantially rectangular corresponding to the shape of the spaces 50*s* and tab walls. FIG. 233 illustrates that the forward member 525 can have an angled configuration (shown as tapering inward from top to bottom) with the tabs 50*t* defining spaces 50*s* that have a mating tapered configuration. The tabs 50*t* and spaces 50*s* can be formed directly on the dose container disk 30 or on another component that communicates with the disk 30 (an upper airway disk 50 is not required).

FIG. 22A shows the piercer carriage 505 with the forward member 525 extending in and/or through space 50*s* to position the piercer 520 over a dose container 30*c* on an outer row 31. FIG. 22B shows the piercer carriage 505 with the forward member 525 stopped by a tab 50*t* to position the piercer 520 over a dose container 30*c* on an inner row 32.

Figure 26:
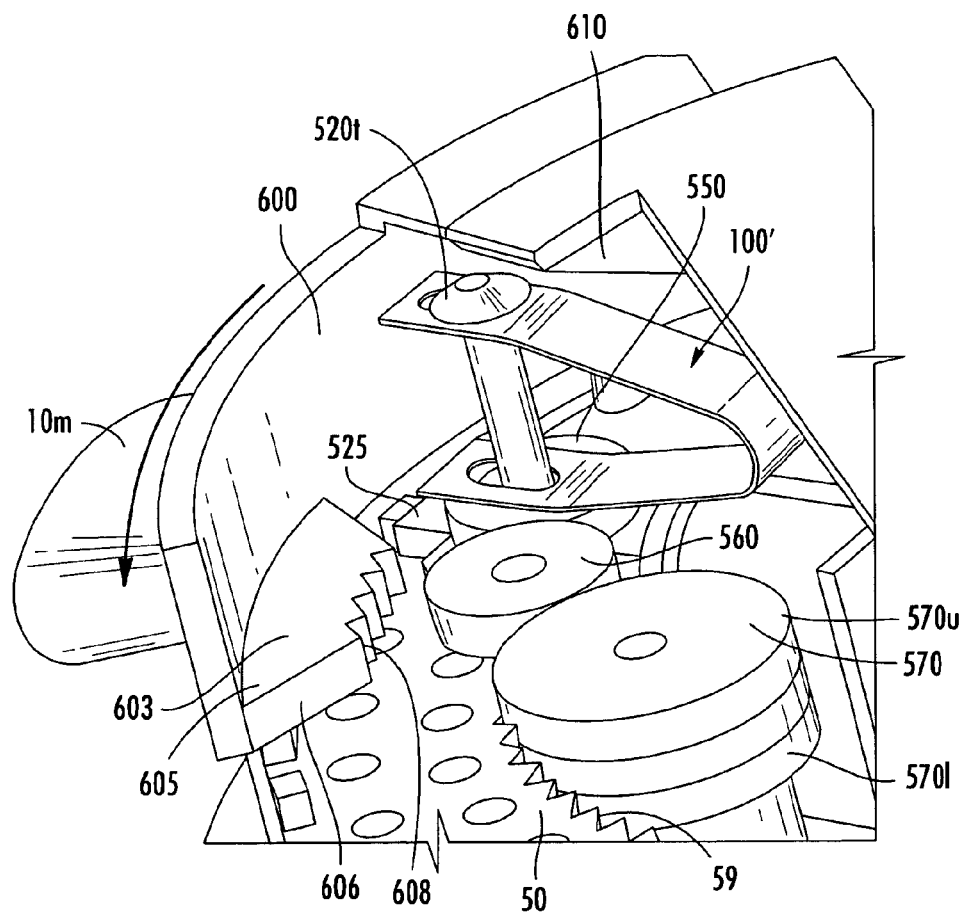
FIG. 26 is a partial cutaway side perspective view of an inhaler and piercing mechanism according to some embodiments of the present invention.

Referring to FIGS. 24 and 26, as shown, the inhaler 10 can include a plurality of cooperating gears, a drive gear 550, an idler gear 560, and a clutch assembly gear 570. This configuration provides a moving gear train plus a one-way clutch for indexing. The clutch assembly gear 570 includes a lower gear 570*l* that communicates with an upper gear 570*u*. As discussed above, the drive gear 550 can be held by the platform 506. The idler gear 560 is in communication with the drive gear 550. The idler gear 560 is in communication with the clutch assembly gear 570 when the piercing carriage 505 is not aligned with either the inner or outer row of dose containers or is not in a piercing position. FIG. 24 illustrates the idler gear 560 meshes with a larger gear on the clutch assembly 570 when the piercer carriage is biased to an inward limit. FIGS. 22A and 22B illustrates that the idler gear 560 does not mesh with the clutch assembly gear 570 when the piercer carriage 505 is in the piercing positions.

Figure 27:
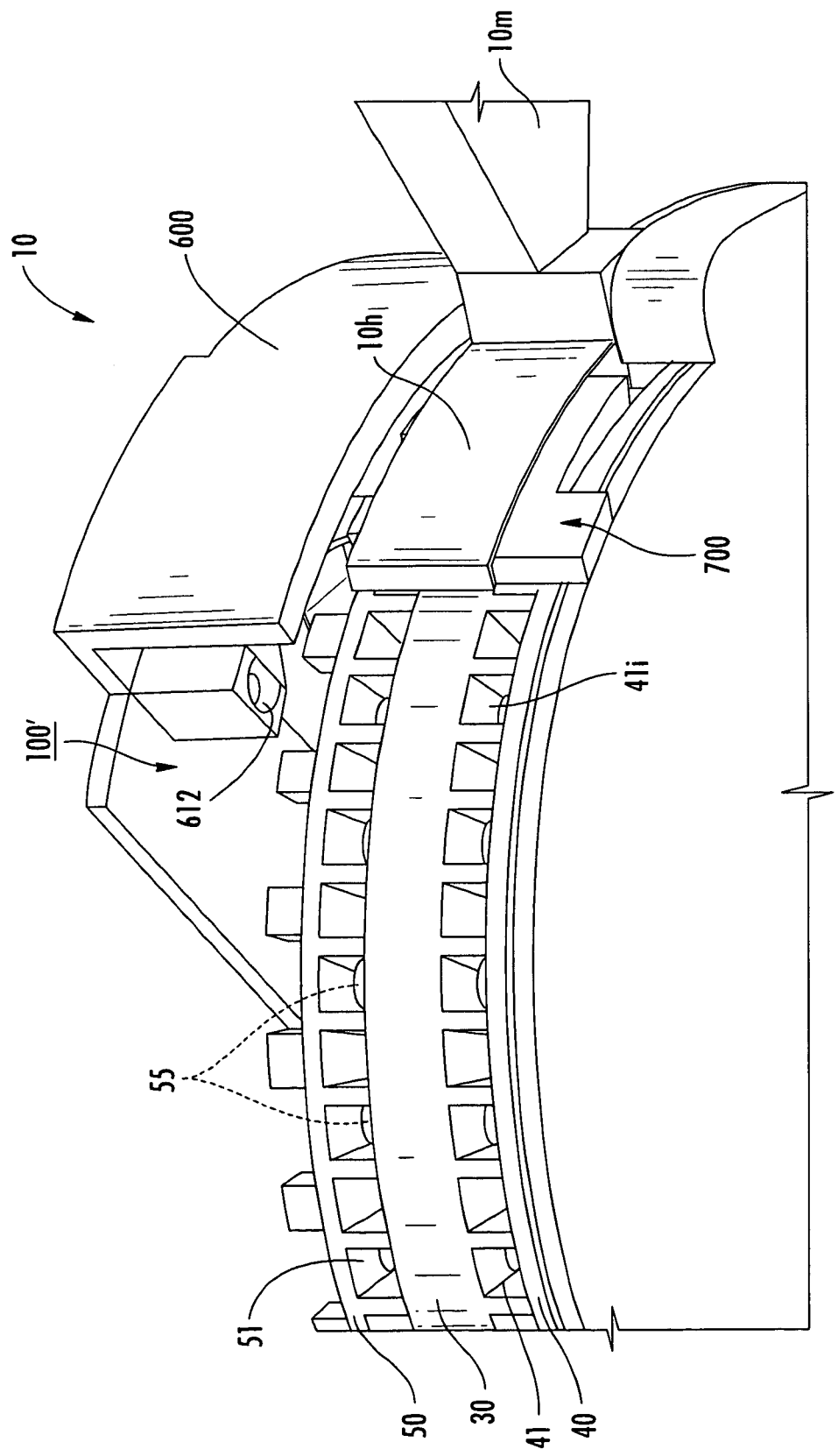
FIG. 27 is a partial cutaway bottom perspective view of the inhaler shown in FIGS. 22A and 22B according to some embodiments of the present invention.
Figure 29:
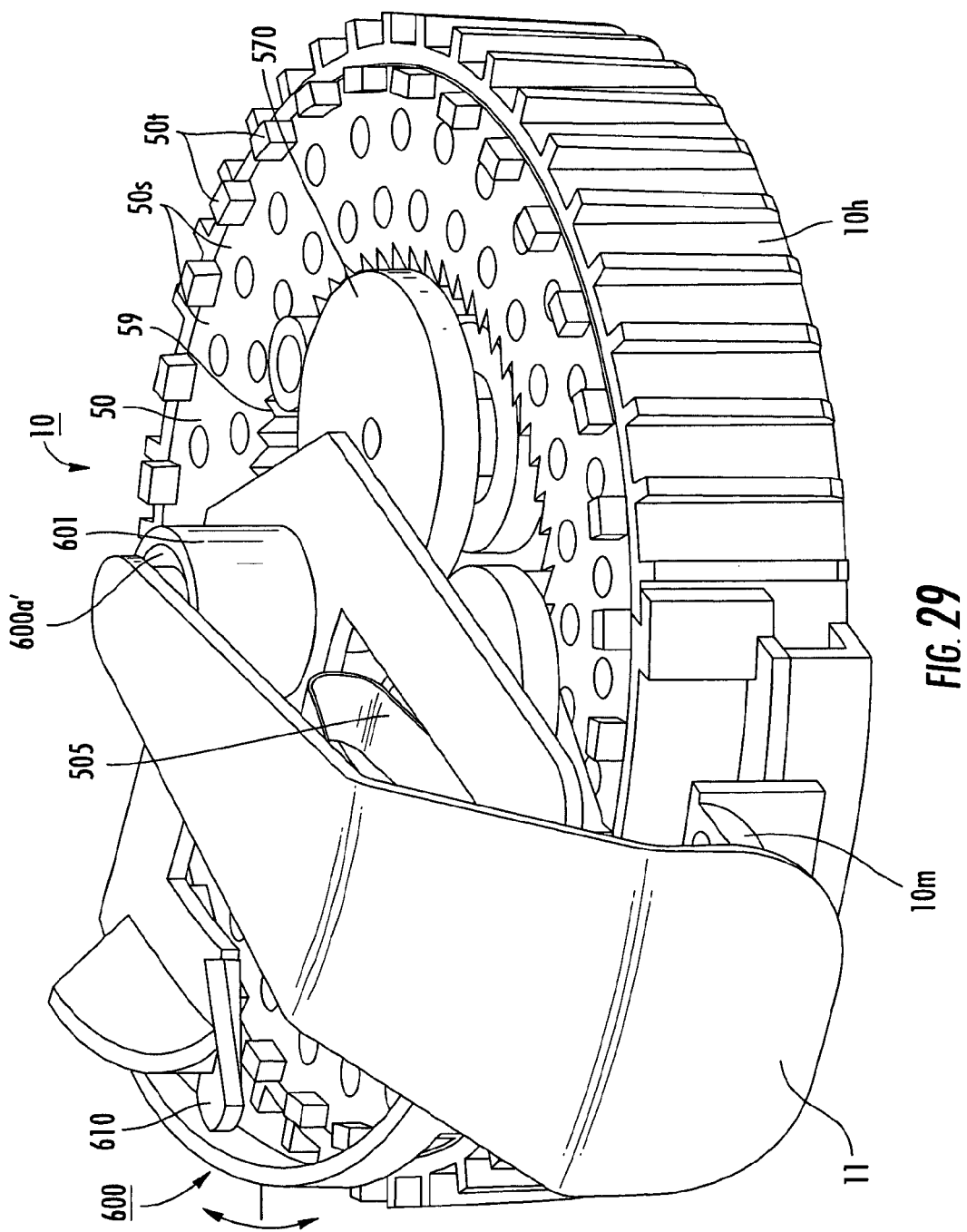
FIG. 29 is partial cutaway perspective end view of an inhaler according to some embodiments of the present invention.

Referring to FIG. 25A, the actuation member 600 rotates from a home to an extended position to move a cam surface 605 associated with the member 600. The cam surface 605 moves (e.g., pushes and/or rotates) the drive gear 550. When the drive gear 550 is in contact with the cam surface 605 as shown in FIG. 25A, teeth on the shelf 603 and/or cam 608 (FIG. 26) rotate the drive gear 550 to cause indexing. When the actuation member 600 returns to a home position, slippage of the upper gear 570*u* with respect to an underlying clutch gear 570/(FIG. 24) of the clutch gear assembly 570 prevents reverse indexing. The actuation member 600 can include a piercing ramp 610 that is circumferentially spaced apart from the cam surface 605 as shown in FIG. 29. FIG. 27 illustrates that the piercing ramp 610 can include a detent recess 612 that the top of the piercer 520*t* can reside (nest) in. The detent recess 612 can be placed in the flat surface at the end of the ramp 610.

Referring to FIG. 26, upon rotation of the actuation member, the shelf 603 can push the carriage 505 inward and the teeth on the shelf can allow the indexing of the dose container. Following indexing of the dose disk 30 and/or assembly 20, the piercer carriage 505 is released to a rest position based on the position of the disk 30 and/or disk assembly 20 in the inhaler housing 10*h*. Continued actuation of the actuation member 600 (e.g., continued rotation to an extended position) causes the actuation member 600 to continue to rotate to position the piercing ramp 610 over the piercer carriage 505 (FIG. 29). The piercer 520 is pushed downward based on contact with the ramp 610 to pierce the sealants (see, e.g., FIG. 18A). The top of the piercer 520*t* can be held in the detent recess 612 shown in FIG. 27. The piercer 520 can have a pierce-and-stay or pierce-and-retract (at least partially retract) operational protocol. The detent operation/feature can provide tactile or audible feedback to a user. The indexing and/or radial movement of the piercer can be in response to the stroke of the actuation member 600 (e.g., lever).

In some embodiments, the ramp 610 can be configured to define a dwell surface. The shelf 603 can index the dose container with gear teeth, then drop or disengage to let the piercer carriage find its home position. Then, the piercer can engage the ramp to pierce, then partially retract and stay in that partially retracted position in response to contact with the dwell surface for a time (during inhalation), then fully retract. However, different piercer configurations may be used such as those described hereinabove.

FIG. 27 also illustrates that a lower portion of the housing 10*h* can include an integral ratchet pawl 700 that engages the inlets/openings 41*i* to the airway channels 41 (shown as lower airway inlets) to prevent reverse rotation or back-up of the dose disk or dose disk assembly 20 during indexing.

Figure 28:
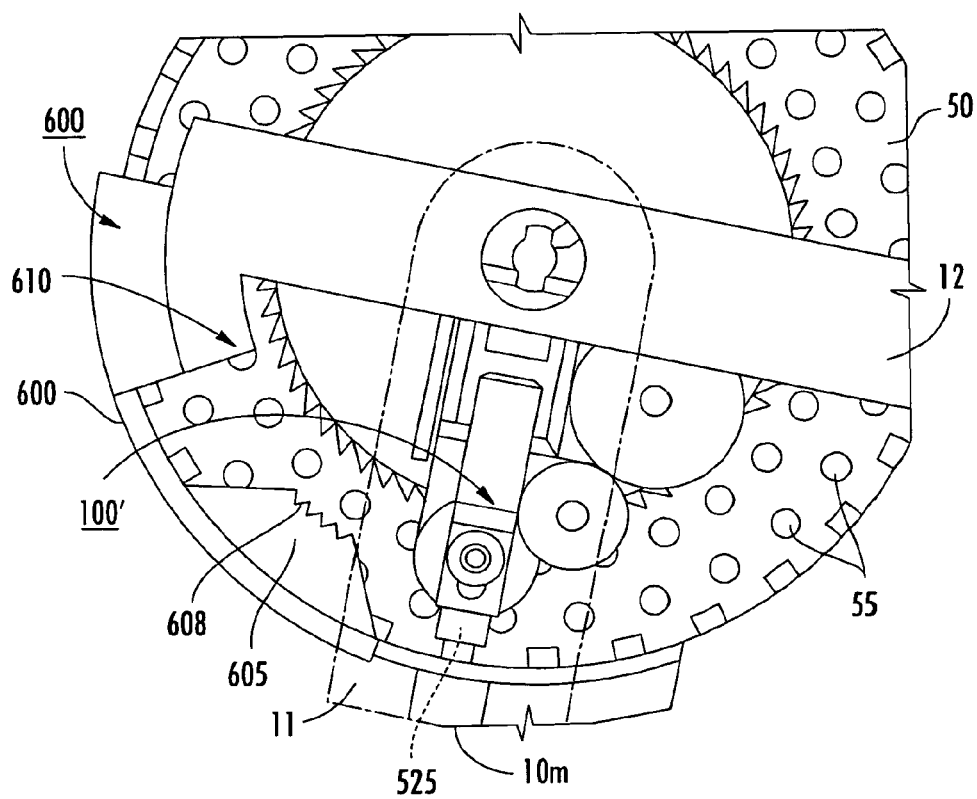
FIG. 28 is a partial cutaway top view of the inhaler shown in FIG. 26 according to some embodiments of the present invention.

FIGS. 28 and 29 illustrate that the mouthpiece cover 11 and the actuation member 600 may be cooperatively attached such that, in some embodiments, the mouthpiece cover 11 can open without moving the actuation member 600, but when the actuation member 600 has moved its full travel, closing of the mouthpiece cover 11 can automatically return the actuation member back to its "home" or start position. The actuation member 600 can be a single component with a semi-circular profile that holds the piercer ramp 610 and a shelf 603 having a cam surface 605 in circumferentially spaced apart relationship. The actuation member 600 can be rotationally mounted to the inhaler 10 and the mouthpiece cover 11 can also be rotationally mounted to the inhaler. The actuation member 600 can include an upwardly extending cylinder 601 with a through aperture 600*a* that allows a mounting extension of the mouthpiece cover 11 to extend therethrough such that the mouthpiece cover 11 and the actuation member 600 have a common (center) rotational axis.

Certain embodiments may be particularly suitable for dispensing medication to respiratory patients, diabetic patients, cystic fibrosis patients, or for treating pain. The inhalers may also be used to dispense narcotics, hormones and/or infertility treatments.

Applicant also reserves the right to claim any of the features or components and methods described and/or shown in the figures including, by way of example, one or more of the following in any combination from the original claims.

(a) An inhaler according to claim 1, wherein the resilient member comprises a spring.

(b) An inhaler according to claim 7, further comprising a ratchet pawl attached to the inhaler housing that serially engages airway ports associated with respective dose containers to prevent the dose container disk assembly from moving in an undesired clockwise or counterclockwise direction.

(c) An inhaler according to claim 1, wherein there are 30 dose container apertures in a first row and 30 dose container apertures in a second row, with a ceiling and floor defined by a flexible sealant.

(d) An inhaler according to claim 1, wherein the piercer comprises a corkscrew piercing head having an operational stroke configured to pierce the sealants with a straight vertical non-rotational movement.

(d) An inhaler according to claim 1, wherein the piercer comprises a fluted piercer (typically with three or four lobes) configured to pierce the sealants. The entry aperture can have a perimeter with a corresponding shape (e.g., three or four lobes, respectively). The fluted piercer may have a twisted lobe configuration and may operate on a straight vertical motion to introduce a full circle opening in the sealants.

(e) An inhaler according to claim 1, wherein the piercer comprises a solid piercer configured to pierce the sealants.

(f) An inhaler according to claim 1, wherein the piercer is configured to seal an aperture in an upper airway disk.

Applicant also reserves the right to claim any other features, or methods supported by the application. For example, the methods may be carried out so that the providing step includes providing the dose container disk sandwiched between an upper and lower airway disk, each airway disk having a plurality of circumferentially spaced apart airway channels with aligned pairs of the upper and lower airway channels defining an airway path for a respective aligned dose container held therebetween, and wherein one of the upper or lower airway disks further comprises a plurality of circumferentially spaced apart piercer apertures, one in communication with a respective one of the dose containers, and wherein the radially retracting and advancing steps both include vertically extending a piercer associated with the piercer mechanism to advance through the piercer aperture, through the upper airway channel and into the lower airway channel, thereby opening the sealants associated with the aligned dose container.

The methods may also include:

leaving the piercer fully extended or partially retracted in the dose container aperture during an inhalation delivery; then fully retracting the piercer; and indexing the dose container disk assembly after the fully retracting step.

The method may be carried out so that the vertically advancing is carried out by contacting the piercer with a ramp that is rotated over a top portion of the piercer to gradually push the piercer down a sufficient distance to pierce the sealants.

The radially advancing and retracting steps may be carried out by radially biasing the piercing mechanism by mounting the piercing mechanism to float above the upper airway disk while in communication with a member that extends outwardly from a medial location of the inhaler to cause the piercing mechanism to slidably reciprocally travel in a radial direction.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An inhaler, comprising:
    an inhaler housing;
    a dose container disk having inner and outer perimeters mounted in the inhaler housing, the dose container disk having a plurality of circumferentially spaced apart dose containers having flexible floor and ceiling sealants attached to the dose container disk holding dry powder therebetween, wherein the dose container disk includes a first row of circumferentially spaced apart apertures at a first radius and a second row of circumferentially spaced apart apertures at a second radius so that the first and second rows are concentric with respect to a center of the disk; and
    a piercer carriage with a piercer mounted in the inhaler housing, the piercer carriage being in communication with a resilient member that radially biases the piercer carriage to radially travel to align the piercer with an underlying or overlying dose container,
    wherein the piercer carriage is configured to serially place the piercer over or under a dose container on the first row then over or under a dose container on the second row whereby the piercer automatically travels sequentially back and forth to alternate between rows and move up or down to pierce the upper and lower sealants residing over and under a respective dose container in the first row, then pierce the sealants residing over and under a dose container in the second row.

2. An inhaler according to claim 1, wherein the piercer carriage comprises a platform that is in communication with the resilient member, and wherein the resilient member resides in the inner perimeter of the dose container disk in a substantially horizontal orientation to bias the piercer carriage radially outward from a center of the disk.

3. An inhaler according to claim 1, wherein the dose container disk has an open center portion, and wherein the resilient member is mounted so as to be aligned with the open center portion of the dose container disk and causes the piercer carriage travel radially outward and inward relative to an upwardly extending centerline of the open space so that the piercer is able to serially pierce the sealants associated with different dose containers on the different rows.

4. An inhaler according to claim 1, wherein the dose container disk comprises or is operably associated with a plurality of circumferentially spaced apart upwardly or downwardly extending tabs, and wherein the piercer carriage is configured to cooperate with the tabs to align the piercer with a target underlying dose container.

5. An inhaler according to claim 1, further comprising:
    a mouthpiece attached to or formed in the inhaler housing,
    a mouthpiece cover that is rotatably attached to the inhaler housing; and
    an actuation member that is rotatably attached to the inhaler housing, wherein the actuation member has a defined operative stroke cycle with a home and a fully extended position and, in operation, the actuation member causes the dose container disk to rotate a defined distance to place a dose container in an indexing position when moved to the fully extended position, and wherein, when the mouthpiece cover opens, the actuation member does not automatically index the dose container disk but after or when the actuation member moves to the fully extended position, closing of the mouthpiece cover causes the actuation member to return to the home position.

6. An inhaler according to claim 1, further comprising an actuation member in communication with a piercing ramp and a circumferentially spaced apart inwardly facing shelf residing in the inhaler housing, wherein the actuation member is rotationally mounted to the inhaler housing to (a) move the shelf to be in position with the piercer carriage to push the piercer carriage inward and index the dose container, then (b) move the piercing ramp to reside above the piercer to force the piercer down to pierce the ceiling and floor sealants to thereby open an aligned dose container.

7. An inhaler according to claim 6, wherein the shelf defines a cam and gear teeth, wherein the shelf gear teeth communicates with a gear in communication with the dose container disk to rotate the dose container disk in the inhaler housing.

8. An inhaler according to claim 1, wherein the piercer carriage is configured to place the piercer over a dose container on the first row then over a dose container on the second row whereby the piercer automatically travels down to pierce sealants over and under a respective dose container in the first row, then pierce sealants over and under a dose container in the second row.

9. An inhaler according to claim 1, wherein the piercer is configured as one of the following:
 (a) a fluted three or four lobe piercer;
 (b) a solid substantially constant diameter piercer that merges into a sharp tip; or
 (c) a corkscrew piercer that travels downward without rotation.

10. An inhaler, comprising:
 an inhaler housing;
 a dose container disk having inner and outer perimeters mounted in the inhaler housing, the dose container disk having a plurality of circumferentially spaced apart dose containers with dry powder therein; and
 a piercer carriage with a piercer mounted in the inhaler housing, the piercer carriage being in communication with a resilient member that radially biases the piercer carriage to radially travel to align the piercer with an underlying or overlying dose container,
 wherein the piercer carriage comprises a platform that resides over or under the dose container disk and communicates with the resilient member, wherein the platform comprises an aperture extending therethrough, wherein the piercer carriage comprises a second resilient member residing above or below the platform, and wherein, in operation, the second resilient member compresses and pushes against the piercer causing the piercer to travel down or up through the platform aperture to pierce at least one sealant associated with a respective dose container.

11. An inhaler according to claim 10, further comprising an actuation member in communication with the piercer carriage, the actuation member comprising a downwardly extending ramp, wherein actuation of the actuation member causes the ramp to contact a top portion of the piercer causing the piercer to travel downward through the platform aperture and open a dose container residing thereunder, and wherein a top portion of the piercer engages a detent recess residing at an outer portion of the ramp to thereby hold the piercer in a partially retracted position.

12. An inhaler, comprising:
 an inhaler housing;
 a dose container disk having inner and outer perimeters mounted in the inhaler housing, the dose container disk having a plurality of circumferentially spaced apart dose containers with dry powder therein; and
 a piercer carriage with a piercer mounted in the inhaler housing, the piercer carriage being in communication with a resilient member that radially biases the piercer carriage to radially travel to align the piercer with an underlying or overlying dose container,
 wherein the dose container disk corn rises or is operably associated with a plurality of circumferentially spaced apart upwardly or downwardly extending tabs, and wherein the piercer carriage is configured to cooperate with the tabs to align the piercer with a target underlying dose container,
 wherein the dose container disk comprises an inner and an outer row of circumferentially spaced apart dose containers, wherein the tabs have a width "W1" and are spaced apart a width "W2", wherein the piercer carriage has a forward member with a width "W3", wherein W3 is less than W2, and wherein, in operation, the forward member is configured to push against one of the tabs to align the piercer with a dose container on the inner row of the dose container disk and when the dose container disk rotates a defined circumferential distance, the piercer forward member enters a space between adjacent tabs to align the piercer with a dose container on the outer row of the dose container disk.

13. An inhaler according to claim 12, wherein the dose containers comprise a flexible ceiling sealant layer and flexible floor sealant layer that seal opposing sides of a dose container aperture with the dry powder held therein.

14. An inhaler, comprising:
 an inhaler housing;
 a dose container disk having inner and outer perimeters mounted in the inhaler housing, the dose container disk having a plurality of circumferentially spaced apart dose containers with dry powder therein;
 a piercer carriage with a piercer mounted in the inhaler housing, the piercer carriage being in communication with a resilient member that radially biases the piercer carriage to radially travel to align the piercer with an underlying or overlying dose container, wherein the dose container disk comprises or is operably associated with a plurality of circumferentially spaced apart upwardly or downwardly extending tabs, and wherein the piercer carriage is configured to cooperate with the tabs to align the piercer with a target underlying dose container;
 an actuation member in communication with a piercing ramp and a circumferentially spaced apart inwardly facing shelf residing in the inhaler housing, wherein the actuation member is rotationally mounted to the inhaler housing to (a) move the shelf to be in position with the piercer carriage to push the piercer carriage inward and index the dose container, then (b) move the piercing ramp to reside above the piercer to force the piercer down to open an aligned dose container; and
 a gear train in the inhaler housing, the gear train comprising a drive gear held by a platform of the piercer carriage, an idler gear in communication with the drive gear, and a clutch assembly gear in communication with the idler gear, wherein the drive gear engages the gear teeth of the actuation member shelf to rotate the drive gear, and the clutch assembly gear is in communication with gear teeth operably associated with the dose container disk, so that, in operation, the drive gear rotates the idler gear, and which, in turn, when engaged with the clutch assembly gear, rotates the clutch assembly gear that rotates the dose container disk to thereby index a dose container into an inhalation position in the inhaler; and optionally wherein the clutch assembly gear selectively engages the idler gear only when the piercer is not in a piercing position, and wherein the clutch gear assembly is configured to slip when the actuation member returns to the home position to prevent reverse indexing.

15. A method of operating an inhaler, comprising:

providing a dose container ring having a plurality of dose containers in radially spaced apart concentric inner and outer rows, the dose containers having respective dose container apertures and upper and lower sealant layers over and under the dose container apertures with dry powder held therebetween;

rotating the dose container ring to present a respective dose container in a dispensing position in the inhaler;

radially advancing a piercing mechanism a distance to align a piercer over a dose container in the outer row;

opening both sealant layers of the aligned dose container to release a first dose of dry powder after the radially advancing step;

subsequently radially retracting the piercing mechanism to align the piercer over a dose container in the inner row; and opening both sealant layers of the aligned dose container to release a second dose of dry powder from the dose container after the radially retracting step, wherein the radially advancing and retracting steps are serially performed so that the piercing mechanism sequentially travels back and forth to alternate between opening a dose container in the outer row then the inner row.

* * * * *

UNITED STATES PATENT AND TRADEMARK OFFICE
CERTIFICATE OF CORRECTION

PATENT NO. : 8,887,722 B2
APPLICATION NO. : 13/063527
DATED : November 18, 2014
INVENTOR(S) : Ruckdeschel et al.

It is certified that error appears in the above-identified patent and that said Letters Patent is hereby corrected as shown below:

In the Claims:
Column 301, Claim 12, Line 10: Please correct "disk corn rises or is"
to read -- disk comprises or is --

Signed and Sealed this
Twenty-eighth Day of April, 2015

Michelle K. Lee
*Director of the United States Patent and Trademark Office*